United States Patent
Smith et al.

(10) Patent No.: US 11,759,350 B2
(45) Date of Patent: Sep. 19, 2023

(54) METHODS AND APPARATUSES FOR MANIPULATING TEMPERATURE

(71) Applicant: EMBR Labs Inc., Boston, MA (US)

(72) Inventors: Matthew J. Smith, Cambridge, MA (US); Samuel Shames, Cambridge, MA (US); Michael A. Gibson, Boston, MA (US); David Cohen-Tanugi, Somerville, MA (US)

(73) Assignee: EMBR Labs IP LLC, Boston, MA (US)

( * ) Notice: Subject to any disclaimer, the term of this patent is extended or adjusted under 35 U.S.C. 154(b) by 119 days.

(21) Appl. No.: 16/891,821

(22) Filed: Jun. 3, 2020

(65) Prior Publication Data

US 2020/0289315 A1 Sep. 17, 2020

Related U.S. Application Data

(63) Continuation of application No. 16/214,372, filed on Dec. 10, 2018, which is a continuation of application
(Continued)

(51) Int. Cl.
*A61F 7/00* (2006.01)
*G01K 1/143* (2021.01)
(Continued)

(52) U.S. Cl.
CPC ............ *A61F 7/007* (2013.01); *G01K 1/143* (2013.01); *G01K 13/20* (2021.01); *A41D 13/005* (2013.01);
(Continued)

(58) Field of Classification Search
CPC ........ A61F 2007/075; A61F 2007/0035; A61F 2007/0093; A61F 2007/0075;
(Continued)

(56) References Cited

U.S. PATENT DOCUMENTS

| | | |
|---|---|---|
| 1,941,173 A | 12/1933 | Lark-Horovitz |
| 2,715,315 A | 8/1955 | Giardini |

(Continued)

FOREIGN PATENT DOCUMENTS

| | | |
|---|---|---|
| CN | 101444447 A | 6/2009 |
| DE | 3128107 A1 | 2/1983 |

(Continued)

OTHER PUBLICATIONS

International Search Report and Written Opinion for International Application No. PCT/US2014/060100, dated Jan. 27, 2015.
(Continued)

*Primary Examiner* — Cassey D Bauer
(74) *Attorney, Agent, or Firm* — Wolf, Greenfield & Sacks, P.C.

(57) ABSTRACT

Methods and apparatuses for manipulating the temperature of a surface are provided. Devices of the present disclosure may include a thermal adjustment apparatus, such as a controller in electrical communication with one or more thermoelectric materials, placed adjacent to the surface of skin. The device may generate a series of thermal pulses at the surface, for providing an enhanced thermal sensation for a user. The thermal pulses may be characterized by temperature reversibility, where each pulse includes an initial temperature adjustment, followed by a return temperature adjustment, over a short period of time (e.g., less than 120 seconds). The average rate of temperature change upon initiation and upon return may be between about 0.1° C./sec and about 10.0° C./sec. In some cases, the average rate of the initial temperature adjustment is greater in magnitude than the average rate of the return temperature adjustment.

25 Claims, 13 Drawing Sheets

Related U.S. Application Data

No. 14/552,002, filed on Nov. 24, 2014, now Pat. No. 10,182,937, which is a continuation of application No. PCT/US2014/060100, filed on Oct. 10, 2014.

(60) Provisional application No. 61/889,996, filed on Oct. 11, 2013.

(51) Int. Cl.
  *G01K 13/20* (2021.01)
  *A41D 13/005* (2006.01)

(52) U.S. Cl.
  CPC .............. A61F 2007/0035 (2013.01); A61F 2007/0075 (2013.01); A61F 2007/0093 (2013.01)

(58) Field of Classification Search
  CPC ... A61F 7/00–2007/0098; G01K 13/20; G01K 1/143; A41D 13/005
  See application file for complete search history.

(56) References Cited

U.S. PATENT DOCUMENTS

| | | |
|---|---|---|
| 2,798,494 A | 7/1957 | Sukacev |
| 3,971,229 A | 7/1976 | Privas |
| 4,470,263 A | 9/1984 | Lehovec et al. |
| 4,585,002 A | 4/1986 | Kissin |
| 4,640,284 A | 2/1987 | Ruderian |
| D298,458 S | 11/1988 | Margolin et al. |
| 4,860,748 A | 8/1989 | Chiurco et al. |
| 4,930,317 A | 6/1990 | Klein |
| 5,092,129 A | 3/1992 | Bayes et al. |
| 5,097,828 A | 3/1992 | Deutsch |
| 5,097,829 A | 3/1992 | Quisenberry |
| 5,269,369 A | 12/1993 | Faghri |
| 5,374,123 A | 12/1994 | Bu |
| 5,580,350 A | 12/1996 | Guibert et al. |
| 5,628,769 A | 5/1997 | Saringer |
| 5,741,067 A | 4/1998 | Gschwind et al. |
| 5,746,702 A | 5/1998 | Gelfgat et al. |
| 5,800,481 A | 9/1998 | Loos |
| 5,800,490 A | 9/1998 | Patz et al. |
| 5,956,963 A | 9/1999 | Lerner |
| 5,970,718 A | 10/1999 | Arnold |
| 6,023,932 A | 2/2000 | Johnston |
| 6,091,994 A | 7/2000 | Loos |
| 6,125,636 A | 10/2000 | Taylor et al. |
| 6,297,728 B1 | 10/2001 | Rippbauer |
| 6,311,497 B1 | 11/2001 | Chung |
| 6,362,740 B1 | 3/2002 | Jung |
| 6,407,965 B1 | 6/2002 | Matoge et al. |
| 6,426,921 B1 | 7/2002 | Mitamura |
| 6,438,964 B1 | 8/2002 | Giblin |
| 6,679,908 B2 | 1/2004 | Shimizu |
| 6,735,083 B2 | 5/2004 | Lin |
| 6,739,138 B2 | 5/2004 | Saunders et al. |
| 6,748,747 B2 | 6/2004 | Hoschek |
| 6,823,678 B1 | 11/2004 | Li |
| 6,840,955 B2 | 1/2005 | Ein |
| 6,915,641 B2 | 7/2005 | Harvie |
| 6,948,322 B1 | 9/2005 | Giblin |
| 7,037,326 B2 | 5/2006 | Lee |
| 7,186,957 B2 | 3/2007 | Martin |
| 7,189,252 B2 | 3/2007 | Krueger |
| 7,331,183 B2 | 2/2008 | Askew |
| 7,347,060 B2 | 3/2008 | Krempel |
| 7,637,263 B2 | 12/2009 | Fisher et al. |
| 7,713,295 B2 | 5/2010 | Ahn et al. |
| 7,744,640 B1 | 6/2010 | Faries, Jr. et al. |
| 7,816,628 B2 | 10/2010 | Fernandez et al. |
| 7,871,427 B2 | 1/2011 | Dunbar et al. |
| 7,875,791 B2 | 1/2011 | Leonov et al. |
| 8,062,797 B2 | 11/2011 | Fisher et al. |
| 8,083,786 B2 | 12/2011 | Gafni et al. |
| 8,087,254 B2 | 1/2012 | Arnold |
| 8,087,823 B2 | 1/2012 | Aube et al. |
| 8,128,675 B2 | 3/2012 | Nahhas |
| 8,147,533 B2 | 4/2012 | Baxter et al. |
| 8,255,004 B2 | 8/2012 | Huang et al. |
| 8,257,414 B2 | 9/2012 | Kelner et al. |
| 8,267,983 B2 | 9/2012 | Rogers et al. |
| 8,267,984 B2 | 9/2012 | Rogers |
| 8,397,158 B1 | 3/2013 | Vistakula |
| 8,397,518 B1 | 3/2013 | Vistakula |
| 9,849,024 B2 | 12/2017 | Mandel |
| 10,182,937 B2 | 1/2019 | Smith et al. |
| 2004/0059400 A1 | 3/2004 | Lin |
| 2005/0000231 A1 | 1/2005 | Lee |
| 2005/0251120 A1 | 11/2005 | Anderson et al. |
| 2006/0141308 A1 | 6/2006 | Becerra et al. |
| 2007/0193278 A1 | 8/2007 | Polacek et al. |
| 2008/0141681 A1 | 6/2008 | Arnold |
| 2008/0314429 A1 | 12/2008 | Leonov |
| 2009/0221943 A1 | 9/2009 | Burbank et al. |
| 2010/0107657 A1 | 5/2010 | Vistakula |
| 2010/0185267 A1 | 7/2010 | Dickie |
| 2010/0198204 A1 | 8/2010 | Rogers |
| 2010/0198318 A1 | 8/2010 | Rogers |
| 2010/0198322 A1 | 8/2010 | Joseph et al. |
| 2010/0211142 A1 | 8/2010 | Rogers et al. |
| 2010/0216433 A1 | 8/2010 | Storozuk |
| 2011/0071603 A1 | 3/2011 | Moore |
| 2011/0313499 A1* | 12/2011 | Smith .............. A61F 7/007 607/113 |
| 2012/0018418 A1 | 1/2012 | Shantha et al. |
| 2012/0318781 A1 | 12/2012 | Lavin, Jr. |
| 2013/0085552 A1 | 4/2013 | Mandel |
| 2013/0087180 A1 | 4/2013 | Stark et al. |
| 2013/0124866 A1 | 5/2013 | Farrugia et al. |
| 2013/0304165 A1 | 11/2013 | Rogers |
| 2013/0333394 A1 | 12/2013 | Chow |
| 2015/0101788 A1 | 4/2015 | Smith et al. |
| 2017/0056238 A1 | 3/2017 | Yi et al. |
| 2017/0095367 A1 | 4/2017 | Lini |
| 2018/0042761 A1 | 2/2018 | Smith et al. |
| 2019/0117444 A1 | 4/2019 | Smith et al. |

FOREIGN PATENT DOCUMENTS

| | | |
|---|---|---|
| DE | 3905570 A1 | 8/1990 |
| EP | 1001470 A1 | 5/2000 |
| EP | 1227375 A1 | 7/2002 |
| EP | 1737052 A1 | 12/2006 |
| EP | 1854437 A1 | 11/2007 |
| EP | 1679984 B1 | 5/2008 |
| JP | S62-82963 A | 4/1987 |
| JP | S63-229047 A | 9/1988 |
| JP | H11-042282 A | 2/1999 |
| JP | 2004-173750 A | 6/2004 |
| JP | 2008-142108 A | 6/2008 |
| JP | 2009-278575 A | 11/2009 |
| JP | 2012-079095 A | 4/2012 |
| WO | WO 2004/014169 A2 | 2/2004 |
| WO | WO 2004/111741 A1 | 12/2004 |
| WO | WO 2005/081679 A2 | 9/2005 |
| WO | WO 2006/075134 A1 | 7/2006 |
| WO | WO 2008/095851 A2 | 8/2008 |
| WO | WO 2010/085163 A1 | 7/2010 |
| WO | WO 2010/093604 A1 | 8/2010 |
| WO | WO 2010/120909 A1 | 10/2010 |
| WO | WO 2011/150427 A2 | 12/2011 |
| WO | WO 2011/156643 A1 | 12/2011 |
| WO | WO 2012/083151 A1 | 6/2012 |

OTHER PUBLICATIONS

International Search Report and Written Opinion for International Application No. PCT/US2016/022105, dated Aug. 5, 2016.

Arens et al., The Skin's Role in Human Thermoregulation and Comfort. Thermal and Moisture Transport in Fibrous Materials, eds. N. Pan and P. Gibson, Woodhead Publishing Ltd. 2006:560-602.

(56) References Cited

OTHER PUBLICATIONS

De Dear et al., Progress in thermal comfort research over the last twenty years. Indoor Air. 2013;23:442-61.
Parkinson et al., Perception of Transient Thermal Environments: pleasure and alliesthesia. Proceedings of 7th Windsor Conference: The changing context of comfort in an unpredictable world, Cumberland Lodge, Windsor, UK, Apr. 12-15, 2012, 15 pages.
Zhang et al., Thermal sensation and comfort models for non-uniform and transient environments, part III: Whole-body sensation and comfort. Building and Environment. 2010;45:399-410.
[No Author Listed] ASTM C1055-20: Standard guide for heated system surface conditions that produce contact burn injuries. ASTM International, West Conshohocken, PA, 2020:1-8.
Composto et al., Thermal comfort intervention for hot-flash related insomnia in menopausal-aged women: A pilot study. Proceedings of the North American Menopause Society Conference, 2019:24.
Composto et al., Thermal comfort intervention for hot-flash related insomnia symptoms in perimenopausal and postmenopausal-aged women: an exploratory study. Behavioral sleep medicine. Jan. 2, 2021;19(1):38-47.
Davies et al., Facial sensitivity to rates of temperature change: neurophysiological and psychophysical evidence from cats and humans. The Journal of Physiology. Nov. 1, 1983;344(1):161-75.
Filingeri, Neurophysiology of skin thermal sensations. Comprehensive Physiology. Jun. 13, 2016;6(3):1429.
Wang et al., Evaluating the comfort of thermally dynamic wearable devices. Building and Environment. Jan. 1, 2020;167:106443.

\* cited by examiner

METHODS AND APPARATUSES FOR MANIPULATING TEMPERATURE

RELATED APPLICATIONS

This application is a continuation of U.S. application Ser. No. 16/214,372 filed on Dec. 10, 2018, which is a continuation of U.S. application Ser. No. 14/552,002, filed on Nov. 24, 2014, which is a continuation of International Patent Application Serial No. PCT/US2014/060100, filed Oct. 10, 2014, which claims the benefit of priority of U.S. Provisional Patent Application Ser. No. 61/889,996, filed Oct. 11, 2013. Each of these references is incorporated herein by reference in its entirety.

FIELD

The present disclosure relates generally to methods and apparatuses for manipulating temperature of a surface.

BACKGROUND

Substantial amounts of energy are used each year by heating, ventilation and air conditioning (HVAC) systems, for keeping spaces within homes, offices, buildings, and other enclosures within comfortable temperature ranges. Despite the significant amounts of energy expended, thermal discomfort still remains a major cause of dissatisfaction within building environments, largely due to wide variance in personal preference. In many cases, an indoor space considered to be optimally conditioned might only be satisfying to about 80% of the occupants at a given time. Conventional HVAC systems are incapable of providing the spatial and temporal variation in temperature that would be necessary for each occupant to feel comfortable, focused, and productive in his/her respective environment.

Existing wearable devices for thermal regulation (e.g., clothing) are generally passive in that they do not generate or absorb heat but merely serve to insulate the wearer from the outside temperature. Despite rapid improvements in the field of active wearable devices, including watches, accelerometers, motion sensors, etc., there is a gap in the understanding of wearable devices that actively work to enhance the thermal comfort of the wearer.

SUMMARY

Methods and devices for manipulating the temperature of a surface are provided.

In an illustrative embodiment, a device for manipulating a temperature of a surface is provided. The device includes at least one thermoelectric material constructed and arranged to be disposed adjacent the surface. The device also includes a controller in electrical communication with the at least one thermoelectric material, the controller configured to cause the at least one thermoelectric material to generate a thermal pulse at a region of the at least one thermoelectric material adjacent the surface, the thermal pulse including a first temperature adjustment at the region of the at least one thermoelectric material adjacent the surface from a first temperature to a second temperature at a first average rate of between about 0.1° C./sec and about 10.0° C./sec, and a second temperature adjustment at the region of the at least one thermoelectric material adjacent the surface from the second temperature to a third temperature at a second average rate of between about 0.1° C./sec and about 10.0° C./sec, wherein a difference in magnitude between the first temperature and the third temperature is less than 25% of a difference in magnitude between the first temperature and the second temperature.

In another illustrative embodiment, a method for manipulating a temperature of a surface is provided. The method includes positioning a region of at least one thermoelectric material adjacent to the surface; and generating a thermal pulse at the region of the at least one thermoelectric material adjacent the surface. Generating the thermal pulse may include adjusting temperature at the region of the at least one thermoelectric material adjacent the surface from a first temperature to a second temperature at a first average rate of between about 0.1° C./sec and about 10.0° C./sec, and adjusting temperature at the region of the at least one thermoelectric material adjacent the surface from the second temperature to a third temperature at a second average rate of between about 0.1° C./sec and about 10.0° C./sec, wherein a difference in magnitude between the first temperature and the third temperature is less than 25% of a difference in magnitude between the first temperature and the second temperature.

In yet another illustrative embodiment, a device for manipulating a temperature of a surface is provided. The device includes a thermal adjustment apparatus constructed and arranged to be disposed adjacent the surface, the thermal adjustment apparatus configured to generate a thermal pulse over a time period of less than 120 seconds at a region of the temperature adjustment apparatus adjacent the surface, the thermal pulse including a first temperature adjustment at the region of the thermal adjustment apparatus adjacent the surface from a first temperature to a second temperature at a first average rate of between about 0.1° C./sec and about 10.0° C./sec, and a second temperature adjustment at the region of the thermal adjustment apparatus adjacent the surface from the second temperature to a third temperature at a second average rate of between about 0.1° C./sec and about 10.0° C./sec, wherein a difference in magnitude between the first temperature and the third temperature is less than 25% of a difference in magnitude between the first temperature and the second temperature, and a magnitude of the first average rate is greater than a magnitude of the second average rate.

In a further illustrative embodiment, a method for manipulating a temperature of a surface is provided. The method includes positioning a region of a thermal adjustment apparatus adjacent to the surface; and generating a thermal pulse over a time period of less than 120 seconds at the region of the thermal adjustment apparatus adjacent the surface. Generating the thermal pulse may include adjusting temperature at the region of the thermal adjustment apparatus adjacent the surface from a first temperature to a second temperature at a first average rate of between about 0.1° C./sec and about 10.0° C./sec, and adjusting temperature at the region of the thermal adjustment apparatus adjacent the surface from the second temperature to a third temperature at a second average rate of between about 0.1° C./sec and about 10.0° C./sec, wherein a difference in magnitude between the first temperature and the third temperature is less than 25% of a difference in magnitude between the first temperature and the second temperature, and a magnitude of the first average rate is greater than a magnitude of the second average rate.

Various embodiments of the present disclosure provide certain advantages. Not all embodiments of the present disclosure share the same advantages and those that do may not share them under all circumstances. Various embodiments described may be used in combination and may provide additive benefits.

Further features and advantages of the present disclosure, as well as the structure of various embodiments of the present disclosure are described in detail below with reference to the accompanying drawings.

BRIEF DESCRIPTION OF THE DRAWINGS

The accompanying drawings are not intended to be drawn to scale. For purposes of clarity, not every component may be labeled in every drawing. In the drawings.

DETAILED DESCRIPTION

Figure 1A:
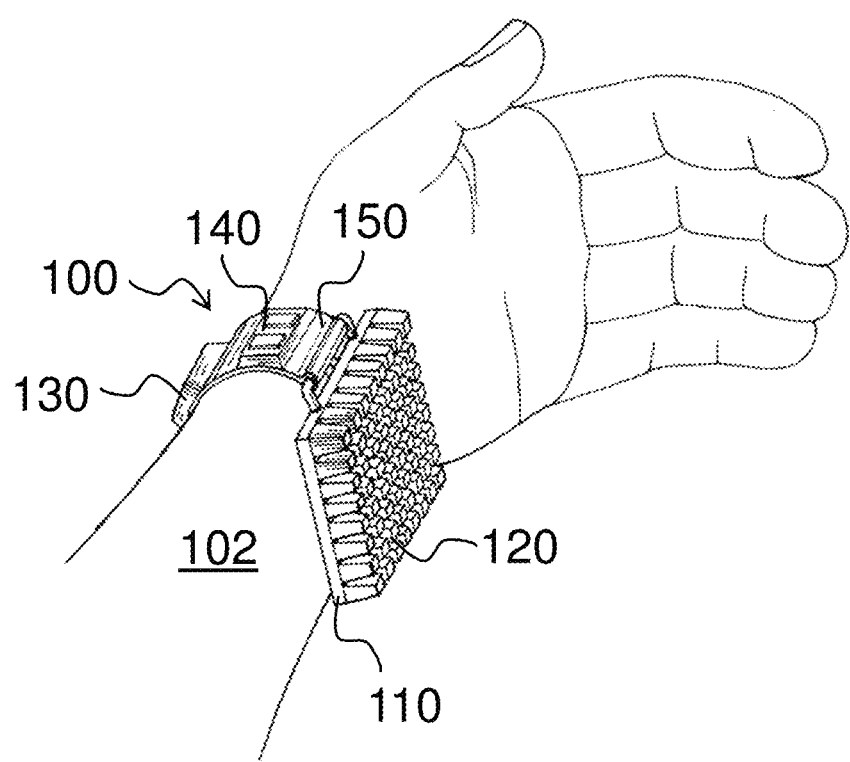
FIG. 1A shows a perspective view of a device for manipulating the temperature of a surface worn by a user according to one set of embodiments.

Methods and apparatuses for manipulating the temperature of a surface are generally provided. The present disclosure relates to a device that includes one or more thermoelectric materials, or other suitable thermal adjustment apparatus(es), placed near a surface, such as the skin of a user. The device may be configured to generate a series of thermal pulses in succession at the surface. This thermal pulsing, when suitably applied, may result in an enhanced thermal sensation for a user which, in some cases, may provide the user with a more pleasurable thermal experience than would otherwise be the case without the thermal pulsing.

As further described herein, a thermal pulse may include a transient, reversible temperature change at a surface, where the temperature changes from an initial temperature to another temperature, quickly followed by a return temperature change at the surface from the other temperature back to the initial temperature, or a temperature close to the initial temperature, all over a relatively short period of time (e.g., less than 120 seconds, or shorter).

For example, a thermal pulse may include a first temperature adjustment at a surface from a first temperature to a second temperature (e.g., at an average rate of 0.1°-10.0° C./sec), and a second temperature adjustment at the surface from the second temperature to a third temperature (e.g., also at an average rate of 0.1°-10.0° C./sec). In such a thermal pulse, the difference in magnitude between the first temperature and the third temperature may be less than 25% of the difference in magnitude between the first temperature and the second temperature. Further, in some cases, the magnitude of the first average rate may be greater than the magnitude of the second average rate.

Under conventional usage, thermoelectric materials, or other temperature adjustment devices, for heating or cooling are generally operated in steady-state, i.e., under constant applied temperature and/or electrical signal modes, so as to maintain long-time scale applications of heating or cooling. For example, such conventional methods are typically used for hot or cold pack compression therapy where it is desirable for the temperature to remain the same for long periods of time. In contrast, aspects of the present disclosure involve generating thermal pulses that are substantially reversible and transient, which may result in continuous thermal stimulation for the human skin.

The inventors have recognized, unexpectedly, that varying the temperature at the surface of human skin in a certain manner, for example, by generating thermal pulses according to particular temperature profiles, may give rise to an enhanced heating or cooling effect for the individual. This enhanced thermal effect may be perceived by the individual in a way that is more pronounced when the temperature is pulsed back and forth in a reversible manner at the surface under short time durations (e.g., less than 120 seconds, less than 30 seconds), in comparison to if the temperature is gradually changed from one temperature to another at the surface over longer periods of time (e.g., over several minutes or hours). That is, when subject to thermal pulses in accordance with embodiments of the present disclosure, the perceived strength of this heating/cooling effect is comparable to actual changes in temperature that are much larger in magnitude and which may be applied, for example, at steady state.

By generating a suitable series of thermal pulses at the surface of human skin, which may or may not include certain variations between pulses, thermoreceptors of the skin may be continuously stimulated. The inventors have appreciated that, in responding to heating and/or cooling at the surface of the skin, thermoreceptors may have a tendency to adapt and, once accustomed to the immediate environment, become desensitized to the initial stimulus. This is analogous to the desensitization of skin to the touch of an external stimuli, such as clothing or some other stimulus to which the senses may become accustomed.

The inventors have discovered, in particular, that by generating thermal pulses at the surface of human skin having particular combinations of parameters, such as rates of temperature change, magnitudes of temperature change, pulse duration, etc., as described in more detail herein, the effects of adaptive desensitization are mitigated or otherwise reduced, and the perceived effects of cooling and/or heating are enhanced. As compared to the desensitization that may occur in a cooled or heated room, the devices described herein may be able to continuously provide a user with an enhanced thermal experience, e.g., a pleasant feeling of cooling and/or heating, according to his/her preferences. As noted above, due to the manner in which the thermal pulse is generated, when the device is in operation, a user may experience, or feel, a temperature sensation that is perceived to be greater in magnitude as compared to the actual magnitude in temperature change of the device at the surface of the skin.

In some embodiments, the thermal adjustment apparatus includes one or more thermoelectric materials that may be positioned directly adjacent to the skin of a user. An electrical signal may be applied to the thermoelectric material(s) so as to manipulate the temperature of the surface of the skin, for example, in the form of a thermal pulse, and/or a plurality of thermal pulses in succession, one after another. Though, it can be appreciated that any suitable thermal adjustment apparatus may be employed; for example, a laser-powered device, convective thermal device, or any other suitable apparatus that may be able to generate a series of thermal pulses.

In various embodiments, each thermal pulse generated by the device may last for a time period of less than 120 seconds (e.g., 1-30 seconds) and may include a first initial temperature adjustment at a region of the thermoelectric material(s) (or suitable thermal adjustment apparatus) adjacent the surface from a first (initial) temperature to a second (pulsed) temperature, and a second return temperature adjustment at the region adjacent the surface, from the second (pulsed) temperature to a third (return) temperature.

For some embodiments, the first temperature adjustment involves a heating step while the second temperature adjustment involves a cooling step. Or conversely, when the first temperature adjustment involves a cooling step, the second temperature adjustment may involve a heating step. That is, the thermal pulse may be characterized by an initial temperature variation followed by a return to a temperature that is substantially the same or close to the initial temperature at the surface. For example, the difference in magnitude between the first (initial) temperature and the third (return) temperature may be less than 25% of a difference in magnitude between the first (initial) temperature and the second (pulsed) temperature.

Each of the first and second temperature adjustments may be characterized by an average rate of between about 0.1° C./sec and about 10.0° C./sec. Though, in some cases, the magnitude of the average rate of the first temperature adjustment is greater than the magnitude of the average rate of the second temperature adjustment. That is, the time period under which the surface adjacent the thermal adjustment apparatus to thermally relax or otherwise adjust from the second (pulsed) temperature to the third (return) temperature may be longer than the time period for the surface to initially step from the first (initial) temperature to the second (pulsed) temperature.

As noted above, temperature profiles at the surface of the skin, in accordance with various embodiments, may provide a person with an enhanced thermal experience, resulting in a perceived heating or cooling sensation for the person. For example, when the ambient temperature is cooler than is otherwise desirable, a user may set the device to a suitable heating mode where a series of thermal pulses generated at the surface of the user's skin cause the user to feel warmer within that environment. Conversely, in an uncomfortably warm ambient environment, the user may set the device to a suitable cooling mode, generating a series of thermal pulses at the surface of the skin so as to cause the user to feel cooler. For each of the heating and cooling modes, the user may also adjust various parameters (e.g., magnitude of temperature change, rate of change, duration of each pulse, steady-state temperature, etc.) based on preference.

As noted above, existing HVAC systems generally require substantial amounts of energy to heat or cool a commercial building. Embodiments of the present disclosure are estimated to significantly reduce energy consumption related to HVAC usage. For example, outfitting a 1,000 person office building with devices as described herein may consume only 5 kWh a day, as compared to 200 kWh which may be required to adjust a particular region of the building by 1° C. Moreover, methods and devices described herein may provide a user with personal control over his/her level of thermal comfort. By providing a more localized manner of control over a person's thermal comfort, office buildings are estimated to be able to save up to 40% of their HVAC energy usage through a generally reduced HVAC load.

The term thermoelectric material is given its ordinary meaning in the art and refers to materials in which a temperature change is generated at a surface of the material upon application of an electric potential (e.g., voltage and corresponding current), in accordance with the thermoelectric effect (e.g., often referred to by other names such as the Peltier, Thomson, and Seebeck effects). Any suitable thermoelectric may be employed, a number of which are described further below. It should be understood that, while a portion of the description herein describes thermoelectric materials, the present disclosure is not limited to thermoelectric materials, and other thermal adjustment apparatuses may be employed where appropriate.

Figure 1B:
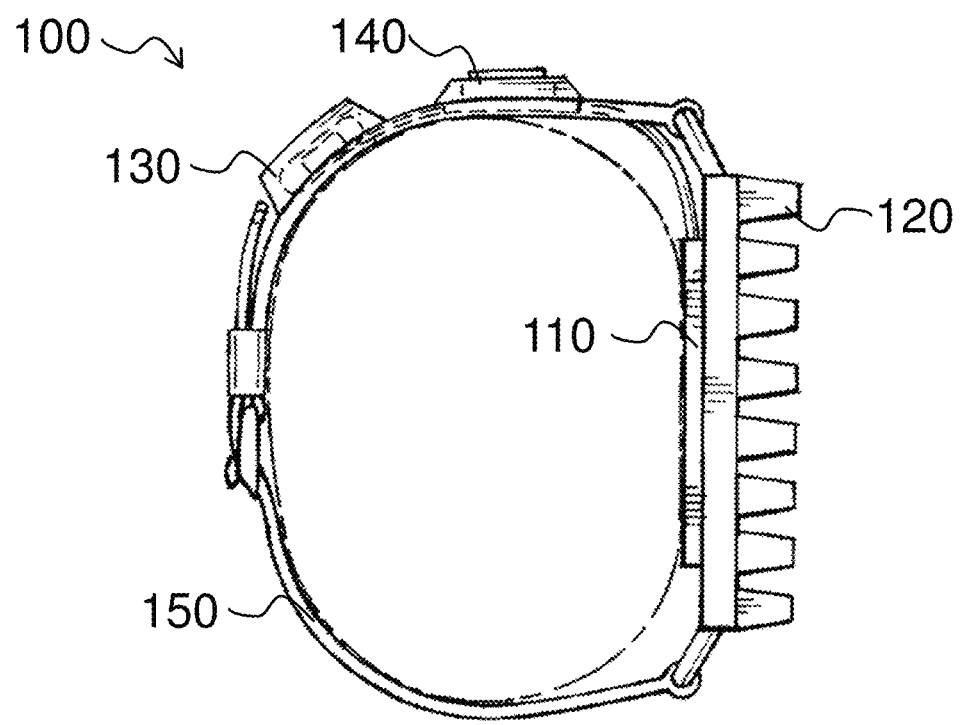
FIG. 1B depicts a side view of the device of FIG. 1A.
Figure 1C:
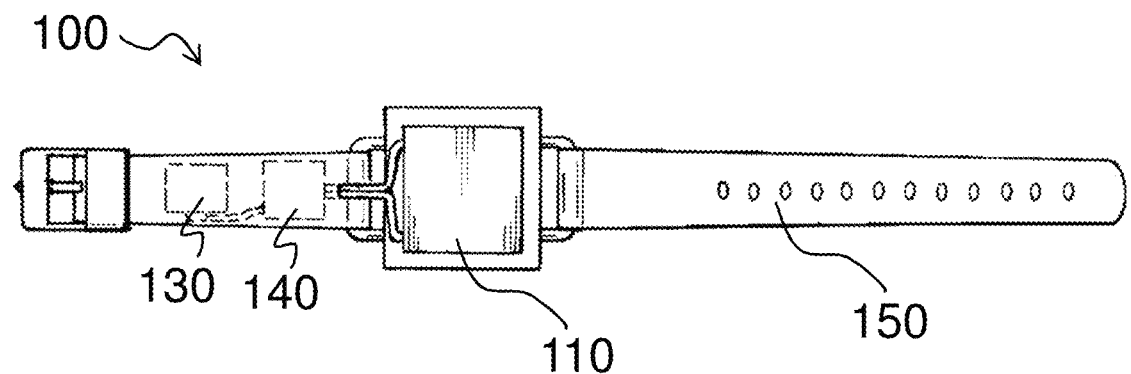
FIG. 1C illustrates a bottom view of the device of FIGS. 1A-1B.

FIGS. 1A-1C depict an embodiment of a device 100 that includes a thermoelectric material 110 that, during use, is configured to be positioned adjacent to the surface of the user's skin 102. As explained further below, the device may include multiple thermoelectric materials positioned at the surface of the skin. The device 100 may optionally include a thermally conductive material 120 (e.g., heat sink) located on the side of the thermoelectric opposite the skin in a manner that covers the thermoelectric material 110.

The thermally conductive material 120, described further below, may dissipate heat to and/or from the thermoelectric material(s), as desired. The thermally conductive material may include any suitable material, such as metal (e.g., aluminum, copper, stainless steel, etc.), thermally conductive polymer, porous ceramic, or another appropriate material.

Though, in some embodiments, as described further below and illustratively shown in FIGS. 2-3, rather than a thermally conductive material, a thermally insulative material may be located on the side of the thermoelectric opposite the skin, covering the thermoelectric material(s). As also noted herein, and shown in FIG. 10, covering the thermoelectric material(s) with a thermally insulative material may enhance the effects of thermal pulsing at the surface of the skin.

It can be appreciated that it is not required for the thermoelectric material(s) to be covered by a thermally conductive or insulative material. For example, a thermal dissipation apparatus may be spaced from or located adjacent to the thermoelectric material(s), without covering the thermoelectric material(s). Or, the thermally conductive or insulative material may be arranged so as to cover a portion of the thermoelectric material(s).

The thermoelectric may be connected to a power source 130 (e.g., battery, plug-in outlet, etc.) and a controller 140, for applying appropriate signals to the thermoelectric, for manipulating the temperature at the surface of the skin. In some cases, the controller may have, one or more inputs and/or outputs to accommodate user control of the device in a suitable and convenient manner.

Each of the elements of the device, i.e., the thermoelectric material 110, thermally conductive material 120, power source 130 and controller 140, may be suitably held together by an appropriate band 150. In some cases, the band 150 may be flexibly adjustable so as to allow for the thermoelectric material 110 to be comfortably and suitably positioned against or otherwise adjacent the surface of the skin such that thermal pulses generated by the thermoelectric are effective to provide the user with a preferred thermal sensation. Though, for some embodiments, the band 150 may exhibit relatively rigid mechanical behavior, providing support for the overall device. It can be appreciated that the band 150 may have any suitable structure and, in some cases, may have stylistic aspects which may lend the device to be worn as a bracelet, anklet, necklace, etc. The band may include any suitable material, such as, but not limited to, metal, plastic, rubber, leather, synthetic leather, or combinations thereof.

It can be appreciated that while the thermoelectric material(s) may be positioned directly adjacent to a surface of the user's skin, in accordance with aspects of the present disclosure, the thermoelectric material(s) are not required to be in direct contact with the user's skin; for example, an additional layer (not shown in the figures) may be placed between the thermoelectric material(s) and the surface of the skin. For example, a thermally conductive or insulative layer, a protective layer, a support layer (e.g., for added comfort), or another appropriate material.

Figure 2:
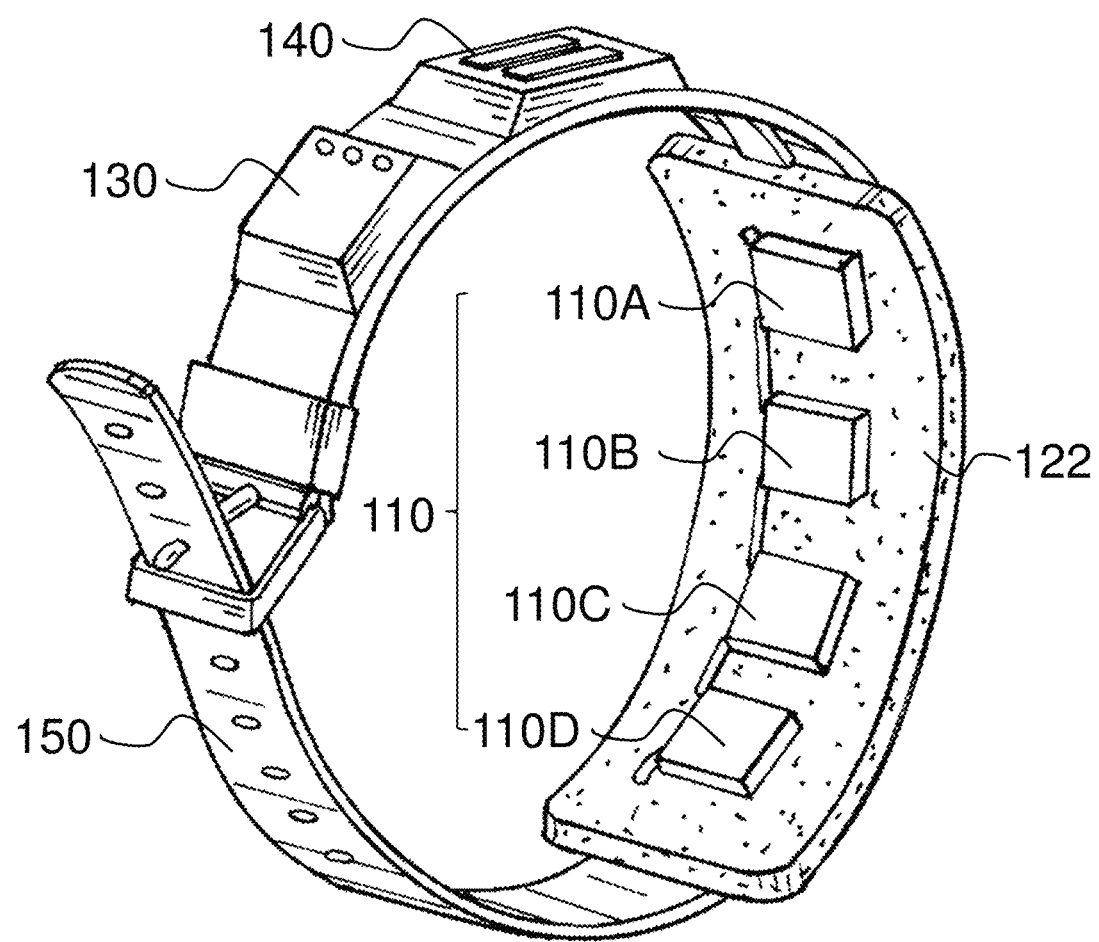
FIG. 2 shows a perspective view of another device for manipulating the temperature of a surface according to one set of embodiments.
Figure 3:
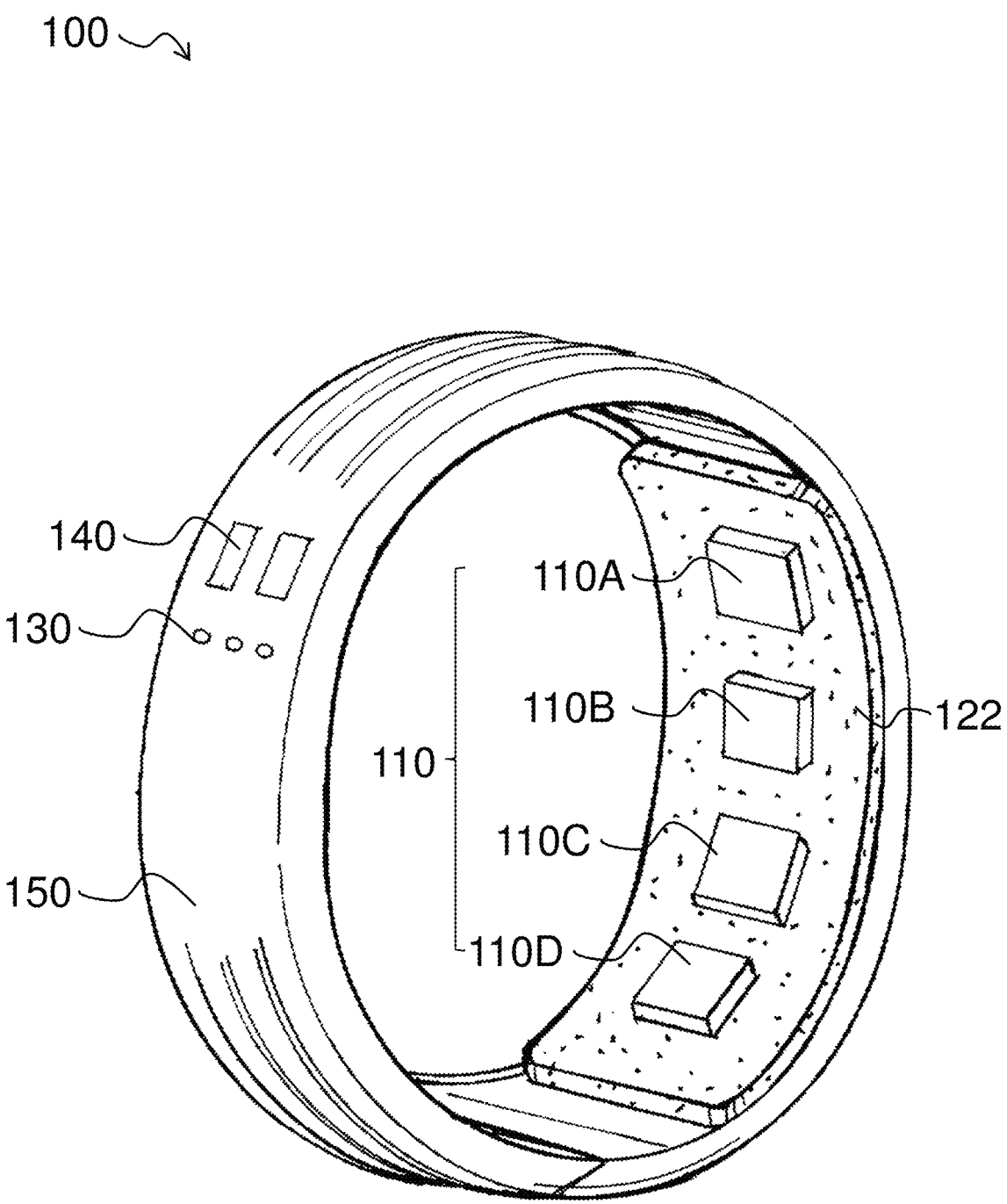
FIG. 3 shows a perspective view of yet another device for manipulating the temperature of a surface according to one set of embodiments.

FIGS. 2-3 show embodiments where the device 100 includes a thermally insulative material 122 located on the side of the thermoelectric opposite the skin, covering the thermoelectric material(s). As a result, the thermally insulative material 122 substantially maintains the overall level of heat generated by the thermoelectric material(s), located at the surface of the skin. In some cases, as discussed further below, the thermally insulative material enhances the effect of the thermal pulses generated by the thermoelectric material(s). The thermally insulative material may include any suitable material, for example, polymer, plastic, elastomer (e.g., rubber, neoprene, etc.), and/or another appropriate material. Such insulative materials may also lend themselves to a device that is less bulky and more flexibility than, for example, if a large heat sink were placed over the thermoelectric material(s). Accordingly, covering the thermoelectric material(s) with a suitable insulative layer such as neoprene, other rubbers or cloth or textile-based materials may allow the device to be more desirable to wear. For some embodiments, the thermoelectric material(s) may be exposed to air, without a covering or other material located thereon.

In some embodiments, the device 100 may include a number of thermoelectric materials. For example, as illustrated in FIGS. 2-3, rather than a single slab of thermoelectric material, the device 100 may include a plurality of smaller thermoelectric materials 110A, 110B, 110C, 110D located adjacent to one another. The thermoelectric materials 110A, 110B, 110C, 110D of FIGS. 2-3 may be sized and arranged in a manner so as to accommodate flexing of the device, for example, around a wrist or other part of the body. Similar to a watch having small rigid components (e.g., metallic parts) that are mutually connected, yet able to flex with respect to one another along the wristband, the plurality of thermoelectric materials may be relatively small, yet arranged in a manner that allows for flexibility and overall wearability of the wristband 150. Accordingly, the relatively small thermoelectric materials may be arranged so as to accommodate the curvature of certain body parts. Thus, the wristband, together with the thermoelectric materials may provide the ability for the device to be adjustably and, hence, snugly fit to the user.

The device may include any suitable number of thermoelectric materials. For example, the device may include 2 or more, 3 or more, 4 or more, 5 or more, 10 or more, etc. such thermoelectric materials. The thermoelectric materials may be arranged in any appropriate pattern along the surface of the device, for example, aligned along a row, arranged in a grid-like formation, positioned in an irregular pattern, arranged to form a particular shape (e.g., ellipse, circular, quadrilateral, hexagonal, etc.), or may be configured in another appropriate way. It may be preferable for the thermoelectric materials to be located in relatively close proximity to one another, so that the cluster of thermoelectrics is able to generate thermal pulses in a suitable manner, for example, thermal pulses that are more concentrated at the surface, so as to elicit a more pronounced response, than if the thermoelectrics are spaced further apart from one another.

In some cases, the thermoelectric materials may be in electrical communication with one another. For example, the thermoelectric materials may be arranged so as to have an electrical connection in series with each other. Accordingly, an electrical signal applied to one of the thermoelectric materials may also be applied to the others to which it is connected. Or, the thermoelectric materials may be electrically isolated from one another, for example, so as to be separately stimulated by a controller, with electrical signals appropriately tailored for each thermoelectric material, for example, at preferred times, magnitudes, and/or rates, as desired.

In some embodiments, not shown in the figures, the device may be incorporated into a fabric (e.g., article of clothing). For example, in certain embodiments, a scarf, necklace, armband, wristband, or any other suitable wearable article may incorporate the device as described herein. The size of the device may be selected, in some embodiments, such that the device fits comfortably on a wrist, on an ankle, within an article of clothing, within the palm of a user's hand, etc.

As noted above, the device may include a controller that is in electrical communication with the thermoelectric material(s), or other appropriate thermal adjustment apparatus. In some embodiments, the controller is configured to apply a series of electrical signals to the thermoelectric material(s) to cause a thermal pulse to be generated at a region of the thermoelectric material(s) adjacent the surface. In some cases, as described further below, the controller may be configured to cause the thermoelectric material(s) to generate a plurality of thermal pulses in succession (e.g., at the region of the thermoelectric material(s) adjacent the surface of the skin of a user). For example, in some embodiments, the thermoelectric material(s) may generate at least one thermal pulse, or at least 2, at least 5, at least 10, at least 20, at least 50, at least 100, at least 200, at least 300, at least 400, or at least 500 thermal pulses in succession, one after another. It can be appreciated that the device may be configured to operate continuously, as there is no limit to how many thermal pulses may be generated at the surface of the skin.

In some embodiments, as noted above, the controller may be in separate electrical communication with each of the thermoelectric materials. As a result, the controller may be configured to cause two or more thermoelectric materials to generate two or more thermal pulses, respectively, that are separate and distinct from one another; for example, a first thermoelectric material generating a first thermal pulse and a second thermoelectric material generating a second thermal pulse. It can be appreciated that various characteristics of the respective thermal pulses may be the same or different. In some embodiments, respective thermal pulses may be generated in a substantially simultaneous manner. Alternatively, for certain embodiments, the first thermal pulse and the second thermal pulse may be generated at different times. Or, as described above, the controller may be configured to cause the thermoelectric material(s) to generate a plurality of respective thermal pulses in succession, in any suitable pattern.

As discussed herein, for some embodiments, the controller is configured to cause the thermoelectric material(s) to produce a number of suitable time-varying, temperature profiles at the surface of human skin, so as to provide an enhanced thermal sensation to the user, which may be tailored to provide the user with a greater degree of thermal comfort and pleasure. Without wishing to be bound by theory, in some cases, the use of multiple thermal pulses may be particularly effective in applying continuous thermal stimulation to the thermoreceptors associated with the skin, as compared to applying a thermal adjustment over a longer steady-state period of time. As noted above, the application of thermal pulses may provide a continuous level of stimulation, which decreases the likelihood for thermoreceptors to become desensitized to thermal variations. As a result, such thermal pulsing may allow the user to experience an overall enhanced perceived thermal feeling. Accordingly, by modulating and/or adjusting the thermal pulses in an appropriate manner, the overall thermal comfort, or perceived comfort, of a user may be manipulated, as desired.

In accordance with aspects of the present disclosure, the device may be configured to generate thermal pulses having appropriate characteristics. For example, the thermal pulse(s) may include a thermal change (e.g., at the region of the thermoelectric material(s) adjacent the surface of the skin) that is substantially reversible over a short period of time. In some embodiments, as noted above, the thermal change includes a first temperature adjustment of the surface from a first initial temperature to a second pulsed temperature, followed by a second temperature adjustment of the surface from the second pulsed temperature to a third return temperature. In some cases, as discussed above, in keeping with pulses that exhibit thermal reversibility, the magnitude difference between the first and third temperatures may be less than 25% of a magnitude difference between the first and second temperatures.

FIGS. 4A-5B depict schematic examples of a thermal pulse which may, in some cases, include a number of regimes. As illustratively shown, the thermal pulse may include a first regime I, an optional second regime II and a third regime III.

In various embodiments, the first regime I may involve an initial temperature adjustment at a surface from a first temperature $T_1$ to a second temperature $T_2$. The optional second regime II may involve a slight change in temperature at the surface from the second temperature $T_2$ to a modified second temperature $T_2'$. The third regime III may involve a subsequent temperature adjustment at the surface from the second temperature $T_2$, or a modified second temperature $T_2'$ (as shown), to a third temperature $T_3$.

As depicted in the schematic of FIGS. 4A-5B, the first temperature $T_1$ and the third temperature $T_3$ at the surface are shown to be the same, though, it should be understood that the first temperature $T_1$ and the third temperature $T_3$ may differ, though, not significantly. For example, the third temperature $T_3$ may be greater or less than the first temperature $T_1$, yet the difference between the first and third temperatures may be less than 25%, or less. It should understood that the regimes described herein are merely examples of the profile of a thermal pulse, and that other profiles having different behavior and/or regimes may be possible.

As noted above, for the examples provided, the optional second regime II may involve an additional adjustment of the second temperature $T_2$ to a modified second temperature $T_2'$. While FIGS. 4A-5B depict the (initial) second temperature $T_2$ and the modified second temperature $T_2'$ to be the same, it can be appreciated that the second temperature $T_2$ and the modified second temperature $T_2'$ may also differ, as discussed further below. For instance, the modified second temperature $T_2'$ may be greater or less than the (initial) second temperature $T_2$. Or, the modified second temperature $T_2'$ may arise during the optional second regime (rather than at the end), as the temperature profile within this regime may be non-linear. That is, the maximum temperature of the surface during the thermal pulse may occur at a time in the middle of the optional second regime II.

As discussed herein, a controller may be configured to apply an electrical signal to the thermoelectric material(s), for creating a preferred temperature profile at the surface of the thermoelectric and, hence, the skin. For illustrative purposes, FIGS. 4A-5B also show the corresponding electrical signal (i.e., amount of voltage applied over particular period of time, which may have any suitable profile and is not limited by that specifically shown in the figures) that may be applied from the controller to the corresponding thermoelectric material, variations of which will be discussed in more detail below.

Figure 4A:
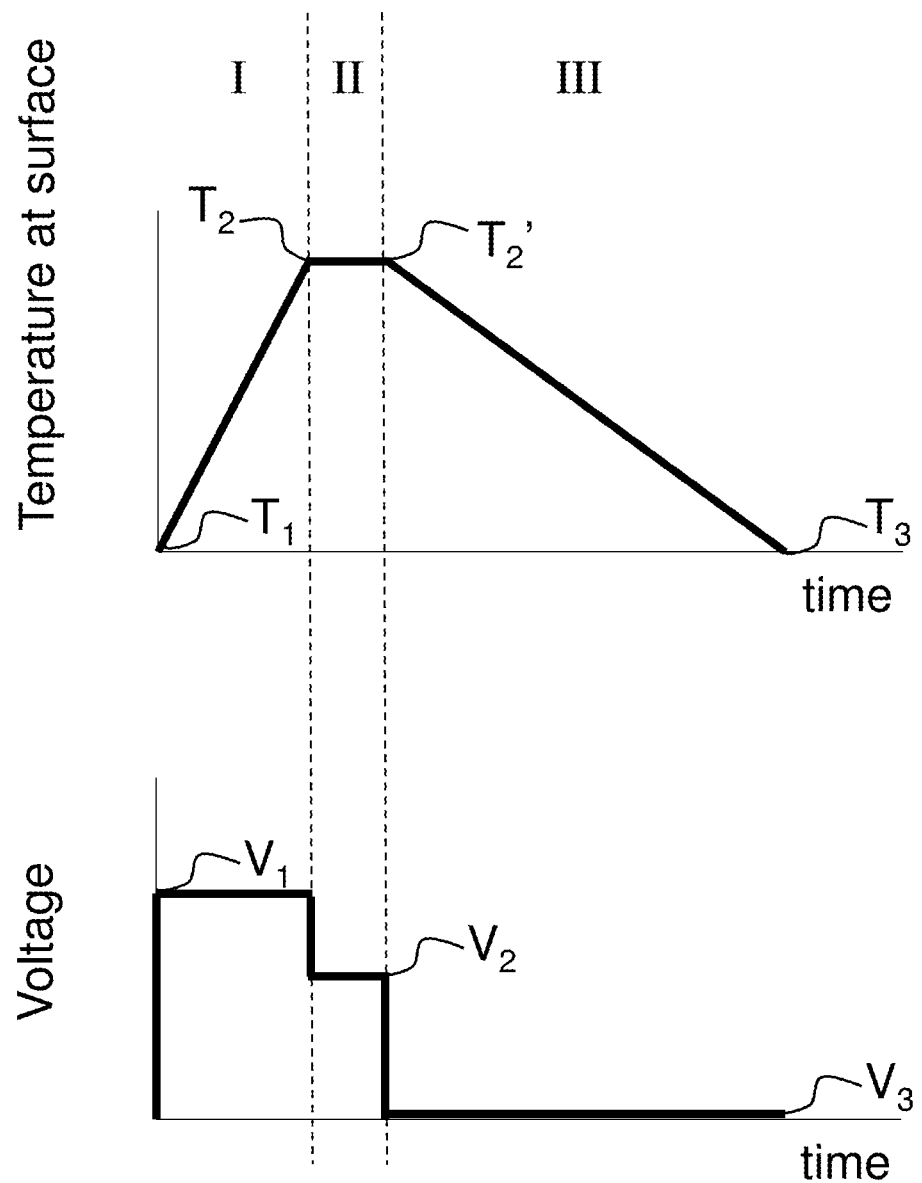
FIG. 4A is a schematic representation of a thermal pulse generated by a device according to one set of embodiments.
Figure 4B:
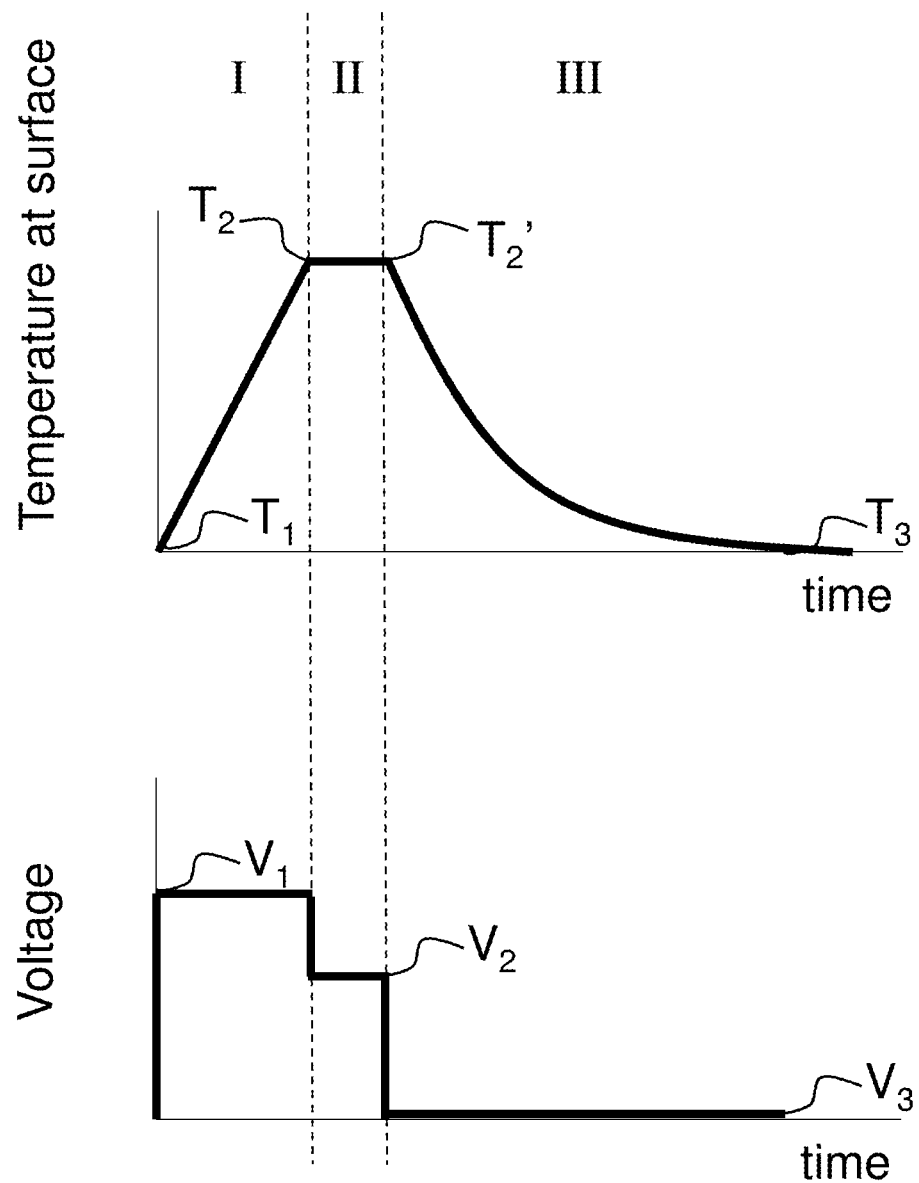
FIG. 4B is a schematic representation of another thermal pulse generated by a device according to one set of embodiments.

In some embodiments, the device (e.g., controller in electrical communication with thermoelectric material(s)) may be configured to generate a heating pulse that gives rise to a perceived heating experience for the user. That is, the user may feel the sensation of being heated (e.g., locally heated at the surface to which the thermal pulsing is applied, or at other regions of the body), while the actual temperature of the body is generally maintained. Such a heating pulse may involve an increase in temperature at the surface of the skin of the user (e.g., region of the thermoelectric material(s) adjacent the surface of the skin), and a subsequent decrease in temperature at the surface of the skin, over a short period of time (e.g., less than 30 seconds, less than 10 seconds). As illustratively shown, FIGS. 4A-4B depict schematic representations of a heating pulse generated at the surface of the skin where the second temperatures $T_2$, $T_2'$ are greater than the first temperature $T_1$ and the third temperature $T_3$.

Figure 5A:
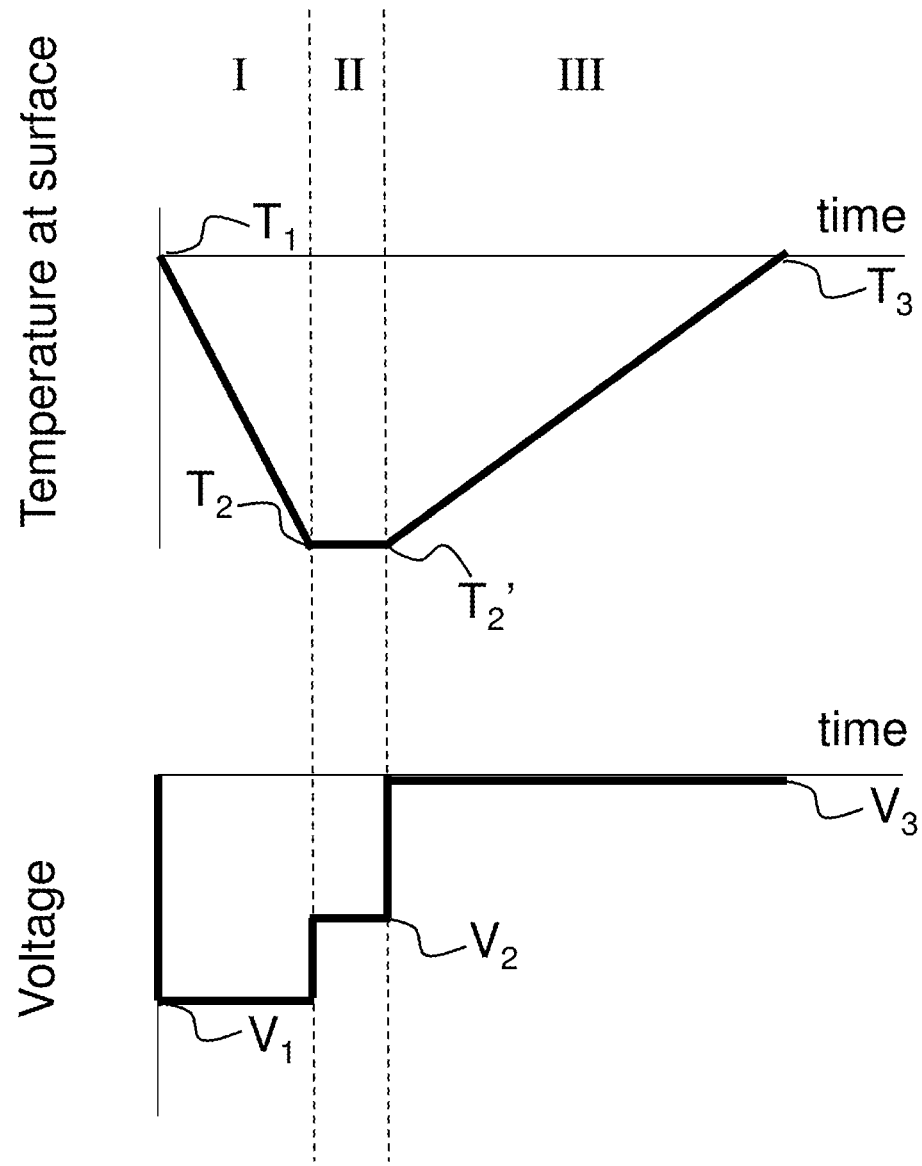
FIG. 5A is a schematic representation of yet another thermal pulse generated by a device according to one set of embodiments.
Figure 5B:
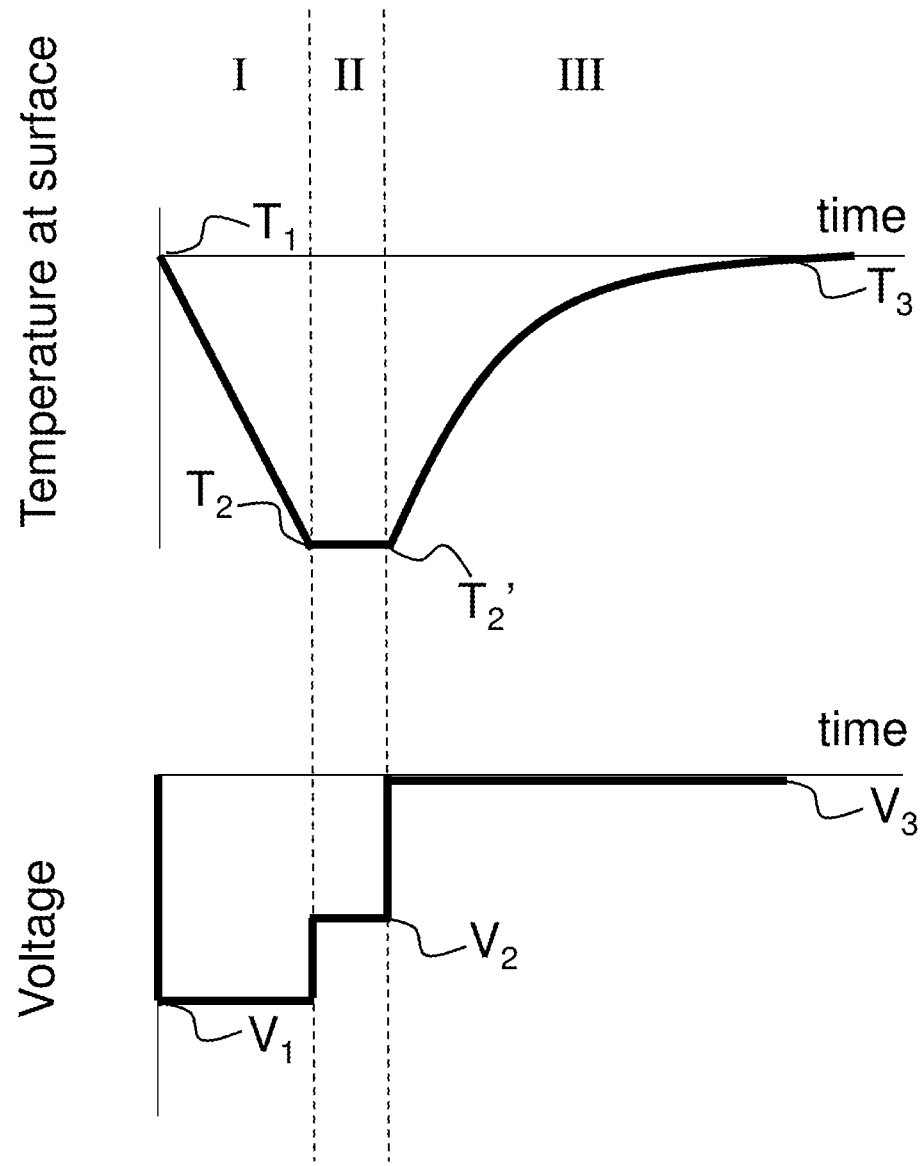
FIG. 5B is a schematic representation of another thermal pulse generated by a device according to one set of embodiments.

Conversely, for some embodiments, the device may be configured to generate a cooling pulse for inducing a perceived cooling effect to the user. Here, similar to the heating experience, the user may feel the sensation of being cooled locally or in other areas of the body, while the actual temperature of the body is generally maintained. The cooling pulse may involve a decrease in temperature at the surface of the skin of the user, quickly followed by an increase in temperature. FIGS. 5A-5B depict schematic representations of a cooling pulse generated at the surface of the skin where the second temperatures $T_2$, $T_2'$ are less than the first temperature $T_1$ and the third temperature $T_3$.

The temperature at a surface may fall within any appropriate range. For example, the first temperature $T_1$ may be room temperature (e.g., ambient temperature), or normothermia (e.g., resting body temperature). In some embodiments, the first temperature $T_1$ is greater than or equal to about 0° C., greater than or equal to about 5° C., greater than or equal to about 10° C., greater than or equal to about 15° C., greater than or equal to about 20° C., greater than or equal to about 22° C., greater than or equal to about 23° C., greater than or equal to about 24° C., greater than or equal to about 25° C., greater than or equal to about 27° C., greater than or equal to about 29° C., greater than or equal to about 30° C., greater than or equal to about 32° C., greater than or equal to about 34° C., greater than or equal to about 35° C., greater than or equal to about 36° C., greater than or equal to about 37° C., greater than or equal to about 38° C., or greater than or equal to about 40° C. In some embodiments, the first temperature $T_1$ is less than about 45° C., less than about 40° C., less than about 38° C., less than about 37° C., less than about 36° C., less than about 35° C., less than about 34° C., less than about 32° C., less than about 30° C., less than about 29° C., less than about 27° C., less than about 25° C., less than about 24° C., less than about 23° C., less than about 22° C., less than about 20° C., less than about 15° C., less than about 10° C., or less than about 5° C. Combinations of the above referenced ranges are also possible (e.g., between about 22° C. and about 29° C., between about 34° C. and about 38° C.). Other temperatures are also possible.

The difference in magnitude between two temperatures (e.g., between the first initial temperature and the second pulsed temperature, between the second pulsed temperature and the third return temperature) may fall within a suitable range. In some cases, where $T_2$ is greater than $T_1$, the difference in magnitude is determined by taking the magnitude of the difference after subtracting $T_1$ from $T_2$. For cases where $T_1$ is greater than $T_2$, the difference in magnitude is determined by taking the magnitude of the difference after subtracting $T_2$ from $T_1$.

In some embodiments, the difference in magnitude between the second (pulsed) temperature $T_2$, or modified second (pulsed) temperature $T_2'$ (whichever is further from the first temperature $T_1$), and the first (initial) temperature $T_1$ is between about 1° C. and about 10° C. As noted above, it can be appreciated that the modified second temperature $T_2'$ is not required to be reached at the end of the optional second regime II. That is, in some cases, the modified second temperature $T_2'$ may be characterized as a temperature within the profile that is furthest from the initial temperature $T_1$. In certain embodiments, the difference in magnitude between whichever of the second temperatures $T_2$, $T_2'$ that is greater in value and the first temperature $T_1$ is greater than or equal to about 1° C., greater than or equal to about 1.2° C., greater than or equal to about 1.4° C., greater than or equal to about 1.5° C., greater than or equal to about 1.6° C., greater than or equal to about 1.8° C., greater than or equal to about 2° C., greater than or equal to about 2.5° C., greater than or equal to about 3° C., greater than or equal to about 4° C., greater than or equal to about 5° C., greater than or equal to about 6° C., greater than or equal to about 7° C., greater than or equal to about 8° C., or greater than or equal to about 9° C. In some embodiments, the difference in magnitude between whichever of the second temperatures $T_2$, $T_2'$ that is greater in value and the first temperature $T_1$ is less than about 10° C., less than about 9° C., less than about 8° C., less than about 7° C., less than about 6° C., less than about 5° C., less than about 4° C., less than about 3° C., less than about 2.5° C., less than about 2° C., less than about 1.8° C., less than about 1.6° C., less than about 1.5° C., less than about 1.4° C., or less than about 1.2° C. Combinations of the above referenced ranges are also possible (e.g., between about 1° C. and about 10° C., between about 1° C. and about 8° C., between about 2° C. and about 8° C., between about 1° C. and about 7° C., between about 1° C. and about 6° C., between about 1° C. and about 3° C.). Other ranges are also possible.

The above discussion with respect to the possible differences in magnitude between the first and second temperatures may also be applicable when considering the difference in magnitude between the second temperature $T_2$, $T_2'$ and the third temperature $T_3$. For example, in some embodiments, the difference in magnitude between the second temperature $T_2$, or modified second temperature $T_2'$ (whichever is further from the first temperature $T_3$), and the third temperature $T_3$ may fall between about 1° C. and about 10° C., certain ranges disclosed above, or other ranges outside of the ranges disclosed.

In some embodiments, the third temperature $T_3$ at the surface of the skin (at the end of a thermal pulse) may approximate the first temperature $T_1$ at the surface of the skin (at the beginning of the thermal pulse). As noted above, it can be appreciated that, in some instances, the first temperature $T_1$ at the surface of the skin, prior to application of a thermal pulse, may be greater or less than the third temperature $T_3$ at the surface of the skin, after application of the thermal pulse.

In some embodiments, the third (return) temperature $T_3$ varies from the first (initial) temperature $T_1$ by a relatively small amount. For example, a difference in magnitude between the first temperature $T_1$ and the third temperature $T_3$ at the surface of the skin may be less than or equal to about 10° C., less than or equal to about 8° C., less than or equal to about 6° C., less than or equal to about 4° C., less or equal to about than about 2° C., less than or equal to about 1° C., less than or equal to about 0.8° C., less than or equal to about 0.5° C., less than or equal to about 0.2° C., or less than or equal to about 0.1° C., or outside of the above noted ranges.

In some embodiments, the third (return) temperature $T_3$ varies from the first (initial) $T_1$ by a small percentage, as compared to the difference between the first temperature $T_1$ and whichever of the second (pulsed) temperatures $T_2$, $T_2'$ that is further from the first temperature $T_1$. For example, the difference in magnitude between the first (initial) temperature $T_1$ and the third (return) temperature $T_3$ at the surface of the skin may be less than or equal to about 25% of the difference in magnitude between the first (initial) temperature $T_1$ and the second (pulsed) temperature $T_2$, $T_2'$, i.e. as determined by the equation $(T_3-T_1)/(T_2-T_1) \times 100\%$, or $(T_3-T_1)/(T_2'-T_1) \times 100\%$ depending on whether the temperature difference between $T_2$ and $T_1$, or $T_2'$ and $T_1$, is greater in magnitude. If the magnitude of $T_2-T_1$ is greater than the magnitude of $T_2'-T_1$, then the former equation is used; though, if the magnitude of $T_2-T_1$ is less than the magnitude of $T_2'-T_1$, then the latter equation is used. In some cases, the difference in magnitude between the first (initial) temperature and the third (return) temperature may be less than or equal to about 25%, less than or equal to about 20%, less than or equal to about 15%, less than or equal to about 10%, less than or equal to about 5%, less than or equal to about 2%, or less than or equal to about 1% of the difference in magnitude between the first (initial) temperature and the second (pulsed) temperature.

In certain embodiments, the first temperature and the third temperature may be about equal (i.e., a reversible thermal pulse) which, in some cases, may occur during steady-state operation of the device. It should be noted that the third temperature $T_3$ may be determined at a time point at which the temperature adjustment between the second temperature $T_2$, $T_2'$ and the third temperature $T_3$ has stopped (e.g., the temperature at the surface of the skin reaches a substantially steady state, or when a new pulse has been initiated). For example, in some embodiments in which the controller is configured to cause the thermoelectric material(s) to generate a plurality of thermal pulses in succession, the third temperature $T_3$ may be determined at the time point when the next thermal pulse begins. Or, in certain embodiments, the third temperature $T_3$ may be determined at a time point at which the temperature has reached a substantially steady state (e.g., the third temperature does not change in magnitude by more than about 5% over 5 seconds).

It can be appreciated that the device may adjust the temperature at the surface of the skin so as to change during various regimes of a thermal pulse, according to a preferred shape or profile. For example, at any given time during the thermal pulse, the temperature profile may exhibit a behavior that is substantially linear, non-linear, exponential (e.g., exponential growth, exponential decay), polynomial (quadratic, cubed, etc.), irregular (e.g., following a piecewise function), or another suitable behavior.

Referring to FIGS. 4A-5B, for some embodiments, the first regime I of the thermal profile may exhibit a substantially linear behavior. That is, for these embodiments, the controller is configured to apply an electrical signal (e.g., square wave voltage) that results in a substantially linear temperature profile over time, for the first regime I. Though, it can be appreciated that other temperature profiles are possible.

In some embodiments, the third regime III of the temperature profile may also exhibit substantially linear behavior, such as that shown in FIGS. 4A and 5A. That is, in some embodiments, the thermal pulse generated by the thermoelectric material(s), or other thermal adjustment apparatus, may be characterized by at least a portion of the temperature adjustment at the surface of the skin exhibiting a behavior between one of the second temperatures $T_2$, $T_2'$ and the third temperature $T_3$ that is substantially linear over time.

Though, for certain embodiments, the temperature adjustment at the surface of the skin between one of the second temperatures $T_2$, $T_2'$ and the third temperature $T_3$ may exhibit a behavior that is not substantially linear over time. For example, as illustrated by FIGS. 4B and 5B, at least a portion of the temperature adjustment at the surface of the skin from the thermal pulse between the second temperature $T_2$, $T_2'$ and the third temperature $T_3$ may exhibit a substantially exponential decay behavior over time. The phrase "exponential decay" generally refers to a behavior in which the parameter (e.g., temperature) reasonably fits an equation such as $T(t)=T_o e^{-\lambda t}$, where $T(t)$ is the temperature at a given time, t, $T_o$ is the initial temperature, and $\lambda$ is a constant.

Figure 6:
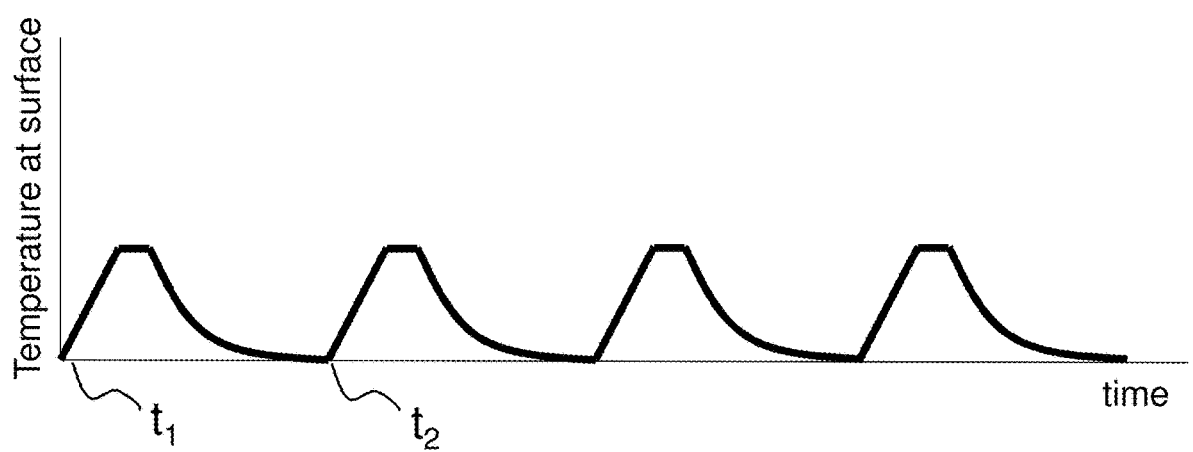
FIG. 6 is a schematic representation of a succession of thermal pulses generated by a device according to one set of embodiments.

In accordance with aspects of the present disclosure, the duration of time of each thermal pulse may suitably vary. The degree of the enhanced thermal sensation and, hence, overall thermal comfort, of a user may depend, at least in part, on the particular duration of the thermal pulse(s), which may be tailored as appropriate. That is, in some cases, a thermal pulse that is too long or too short might not result in a desired level of thermal sensation for a user. The time period may be measured as the time elapsed during a thermal cycle at the surface of the skin from the first temperature $T_1$ to the third temperature $T_3$, as illustrated in FIGS. 4A-5B. For example, as illustrated in FIG. 6, the time period may be measured as the difference between a time point at the start of a first pulse $t_1$ and a time point at the start of a second pulse $t_2$.

In some embodiments, the thermal adjustment apparatus, or controller configured to apply an electrical signal to the thermoelectric material(s), may generate a thermal pulse over a time period of less than or equal to about 120 seconds. In certain embodiments, the time period of an entire thermal pulse from an initial temperature to another, pulsed temperature and substantially returning to the initial temperature (with negligible difference between the initial temperature and the final temperature of the pulse) is less than or equal to about 90 seconds, less than or equal to about 75 seconds, less than or equal to about 60 seconds, less than or equal to about 50 seconds, less than or equal to about 45 seconds, less than or equal to about 40 seconds, less than or equal to about 30 seconds, less than or equal to about 20 seconds, less than or equal to about 15 seconds, less than or equal to about 10 seconds, less than or equal to about 7 seconds, less than or equal to about 5 seconds, less than or equal to about 4 seconds, less than or equal to about 3 seconds, less than or equal to about 2 seconds, or less than or equal to about 1 second. In some embodiments, the time period of a thermal pulse is greater than about 2 seconds, greater than about 3 seconds, greater than about 4 seconds, greater than about 5 seconds, greater than about 6 seconds, greater than about 7 seconds, greater than about 10 seconds, greater than about 15 seconds, greater than about 20 seconds, greater than about 30 seconds, greater than about 40 seconds, greater than about 50 seconds, greater than about 60 seconds, greater than about 75 seconds, or greater than about 90 seconds. Combinations of the above-referenced ranges are also possible (e.g., between about 2 seconds and about 5 seconds, between about 3 seconds and about 10 seconds, between about 10 seconds and about 30 seconds, between about 10 seconds and about 60 seconds, or between about 15 seconds and about 90 seconds). Other ranges are also possible.

Within a thermal pulse, the initial temperature adjustment of the thermal pulse (e.g., regime I shown in FIGS. 4A-5B and 8-9, period in which the temperature at the surface of the skin undergoes a sharp, continuous increase or decrease) may last for a suitable duration. In some embodiments, the initial temperature adjustment of a thermal pulse may last for less than or equal to about 60 seconds, less than or equal to about 50 seconds, less than or equal to about 40 seconds, less than or equal to about 35 seconds, less than or equal to about 30 seconds, less than or equal to about 25 seconds, less than or equal to about 20 seconds, less than or equal to about 15 seconds, less than or equal to about 10 seconds, less than or equal to about 5 seconds, less than or equal to about 4 seconds, less than or equal to about 3 seconds, or less than or equal to about 2 seconds. In some embodiments, the time period of the initial temperature adjustment of a thermal pulse is between about 1 second and about 30 seconds, between about 1 second and about 10 seconds, between about 2 seconds and about 5 seconds, or between about 2.5 seconds and about 4 seconds. Other ranges are also possible.

The temperature adjustment of the thermal pulse on return (e.g., regime III shown in FIGS. 4A-5B and 8-9, period in which the temperature at the surface of the skin undergoes a gradual increase or decrease back toward the initial temperature) may last for a suitable period of time. In some embodiments, the temperature adjustment of the thermal pulse on return may last for less than or equal to about 60 seconds, less than or equal to about 50 seconds, less than or equal to about 40 seconds, less than or equal to about 30 seconds, less than or equal to about 20 seconds, less than or equal to about 10 seconds, or less than or equal to about 5 seconds. In some embodiments, the time period of the temperature adjustment on return may be between about 1 second and about 60 seconds, between about 1 second and about 5 seconds, between about 2 seconds and about 3 seconds, between about 5 seconds and about 30 seconds, between about 5 seconds and about 20 seconds, or between about 5 seconds and about 10 seconds. Other ranges are also possible.

Temperature adjustments of the thermal pulse may exhibit a suitable rate of change of the temperature over time. In some embodiments, the temperature adjustment (e.g., the temperature adjustment from the first initial temperature to the second pulsed temperature, the temperature adjustment from the second pulsed temperature (or the optional modified second pulsed temperature to the third return temperature), the optional temperature adjustment from the second temperature to the modified second temperature) occurs over a particular period of time.

In certain embodiments, the first temperature adjustment (e.g., thermal change on the initial pulse, between the first initial temperature and the second pulsed temperature) occurs over a shorter period of time than the second temperature adjustment (e.g., thermal change on return, between the second pulsed temperature (or the optional modified second pulsed temperature) and the third return temperature). That is, in some embodiments, the magnitude of the average rate of the first temperature adjustment at the beginning of the thermal pulse may be greater than the magnitude of the average rate of the second temperature adjustment at the end of the thermal pulse.

As provided herein, the magnitude of the average rate may be determined by calculating the difference in magnitude between temperature limits (e.g., magnitude of the difference between the first initial temperature and the second pulsed temperature for the first adjustment, magnitude of the difference between the second pulsed temperature and the third return temperature for the second adjustment) and dividing this difference in magnitude between temperature limits by the time over which the temperature is adjusted. As an example, when applying a cooling pulse, if the duration of the first temperature adjustment upon initiation of the pulse is 5 seconds, where the first initial temperature is 28° C. and the second pulsed temperature is 23° C., the magnitude of the average rate of temperature change for this portion of the pulse is 1° C./sec. For the same cooling pulse example, if the duration of the second temperature adjustment upon return of the pulse is 10 seconds, where the second pulsed temperature is 23° C. and the third return temperature is 28° C., the magnitude of the average rate of temperature change for this portion of the pulse is 0.5° C./sec.

In various embodiments, the average rate of the first temperature adjustment, upon initiation of the thermal pulse, between the first initial temperature and the second pulsed temperature, may range between about 0.1° C./sec and about 10.0° C./sec. In some embodiments, the average rate of temperature adjustment on initiation of the thermal pulse is greater than or equal to about 0.1° C./sec, greater than or equal to about 0.2° C./sec, greater than or equal to about 0.3° C./sec, greater than or equal to about 0.5° C./sec, greater than or equal to about 0.7° C./sec, greater than or equal to about 1.0° C./sec, greater than or equal to about 1.5° C./sec, greater than or equal to about 2.0° C./sec, greater than or equal to about 3.0° C./sec, greater than or equal to about 5.0° C./sec, or greater than or equal to about 7.0° C./sec. In certain embodiments, the average rate of the temperature adjustment on initiation of the thermal pulse is less than about 10.0° C./sec, less than about 7.0° C./sec, less than about 5.0° C./sec, less than about 3.0° C./sec, less than about 2.0° C./sec, less than about 1.5° C./sec, less than about 1.0° C./sec, less than about 0.7° C./sec, less than about 0.5° C./sec, less than about 0.3° C./sec, or less than about 0.2° C./sec. Combinations of the above-referenced ranges are possible (e.g., between about 0.1° C./sec and about 10.0° C./sec, between about 0.1° C./sec and about 5.0° C./sec, between about 0.3° C./sec and about 3.0° C./sec, between about 0.3° C./sec and about 1.0° C./sec, between about 0.3° C./sec and about 0.8° C./sec, between about 0.5° C./sec and about 3.0° C./sec). Other ranges are also possible.

The average rate of second temperature adjustment, upon return of the thermal pulse, between the second pulsed temperature and the third return temperature, may fall within a similar range as that of the first temperature adjustment. For example, the average rate of the second temperature adjustment, on return of the thermal pulse, may range between about 0.1° C./sec and about 10.0° C./sec. In various embodiments, the average rate of temperature adjustment on return of the thermal pulse is greater than or equal to about 0.1° C./sec, greater than or equal to about 0.2° C./sec, greater than or equal to about 0.3° C./sec, greater than or equal to about 0.5° C./sec, greater than or equal to about 0.7° C./sec, greater than or equal to about 1.0° C./sec, greater than or equal to about 1.5° C./sec, greater than or equal to about 2.0° C./sec, greater than or equal to about 3.0° C./sec, greater than or equal to about 5.0° C./sec, or greater than or equal to about 7.0° C./sec. In certain embodiments, the average rate of the temperature adjustment on return of the thermal pulse is less than about 10.0° C./sec, less than about 7.0° C./sec, less than about 5.0° C./sec, less than about 3.0° C./sec, less than about 2.0° C./sec, less than about 1.5° C./sec, less than about 1.0° C./sec, less than about 0.7° C./sec, less than about 0.5° C./sec, less than about 0.3° C./sec, or less than about 0.2° C./sec. Other ranges as well as combinations of the above-referenced ranges are also possible.

As discussed herein, in some cases, the average rate of temperature change upon initiation of the pulse may be greater in magnitude than the average rate of temperature change on return of the pulse. In certain embodiments, the magnitude of the average rate of the first temperature adjustment is greater than the magnitude of the average rate of the second temperature adjustment by at least 10%, at least 20%, at least 30%, at least 40%, at least 50%, at least 60%, at least 70%, or at least 80% of the first average rate. In some embodiments, a user may experience an overall increase in thermal sensation, hence, an enhanced level of thermal comfort, as compared to embodiments wherein the first average rate is equal to, or less than, the second average rate of temperature adjustment.

The inventors have recognized that generating thermal pulses that incorporate the above-referenced ranges of average rates of temperature change, and rate differences at certain portions of the thermal pulse, are able to enhance the effects of the thermal pulsing, resulting in the ability to increase levels of localized thermal comfort to the average user. This is in stark contrast to the use of large scale heating or cooling systems (e.g., HVACs, or the like), which are non-localized, and longer term heating or cooling systems (e.g., cold packs, hot packs, or the like), which fail to provide the desired thermal sensation.

As discussed above, the thermal adjustment apparatus may include a controller that applies an appropriate electrical signal to the thermoelectric material(s), for generating the appropriate thermal pulse(s). The electrical signal may include a suitable step up/down in voltage, current, etc.

In some embodiments, the controller includes a voltage source, for generating a suitable electrical signal. In certain embodiments, the voltage source applies a voltage to the thermoelectric material(s) suitable to create a thermal pulse at the surface of the skin of a user. For example, as illustrated in FIGS. 4A-5B, the controller may be configured to apply a first voltage $V_1$, a second voltage $V_2$, and/or a third voltage $V_3$. Though, it can be appreciated that other voltages may be applied in accordance with any appropriate signal pattern. For instance, rather than applying a constant voltage, the electrical signal may employ pulse width modulation, where the width of the pulse is modulated according to a suitable duty cycle (e.g., 10-50% duty cycle), for example, for modulating (and conserving) the power provided to the device. In some cases, pulse width modulation may be applied using suitable duty cycles having relatively short timescales (>100 Hz). Any suitable form of pulse width modulation may be employed.

In some cases, whether the potential that is applied is positive or negative may correspond to whether a heating pulse or cooling pulse is desired. For instance, FIGS. 4A-4B correspond to a heating pulse, where the voltage applied results in an increase in temperature at the surface of the skin. FIGS. 5A-5B, in contrast, correspond to a cooling pulse; here, the voltage applied results in a decrease in temperature at the surface of the skin. Though, it can be appreciated that certain heating or cooling pulses may involve both positive and negative voltages being applied to the thermoelectric material(s) (e.g., via pulse width modulation where voltages are pulsed at an appropriate duty cycle). The average magnitude of a voltage applied to the thermoelectric material(s) at any given point (e.g., first voltage, second voltage, third voltage) may fall within a suitable range. For example, the average magnitude of the voltage applied to the thermoelectric material(s) may be between about 0.1 V and about 10.0 V, between about 1.0 V and about 8.0 V, between about 2.0 V and about 5.0 V, between about 0.1 V and about 5.0 V, between about 0.1 V and about 1.5 V, between about 0.1 V and about 1.0 V, between about 1.0 V and about 3.0 V, between about 3.0 V and about 8.0 V, or any other appropriate range. In some cases, as illustratively shown in FIGS. 4A-5B, the average magnitude of the first voltage may be greater than respective average magnitudes of subsequent voltages (e.g., second voltage, third voltage, etc.) applied during the thermal pulse, for example, to create a sharp temperature adjustment at the surface of the skin from a first initial temperature to a second pulsed temperature. As further shown, the average magnitude of the step voltage applied may drop off, for example, to a second voltage $V_2$ and a third voltage $V_3$, so as to allow for temperature reversibility of the thermal pulse in a manner that is more gradual on return.

As shown in the figures, the third voltage is given by a lack of applied electrical signal, and is depicted to be essentially zero. In some cases, the average magnitude of the third voltage $V_3$ may be substantially non-zero, for example, while also being less than the average magnitude of the first voltage $V_1$ and/or the average magnitude of the second voltage $V_2$. It can be appreciated that, for some embodiments, a voltage (e.g., step voltage) may also be applied in the opposite direction (e.g., negative voltage on return after a positive voltage on initiation of the pulse), so as to elicit a sharper temperature change during the return portion of the thermal pulse. For example, in some embodiments, the first voltage $V_1$ applied to the thermoelectric material(s) may be positive (e.g., during a heating thermal pulse) and the second voltage $V_2$ may be negative (e.g., to cause the temperature at the surface of the skin to decrease more sharply); or vice versa where the first voltage $V_1$ applied to the thermoelectric material(s) is negative and the second voltage $V_2$ is positive.

Figure 8:
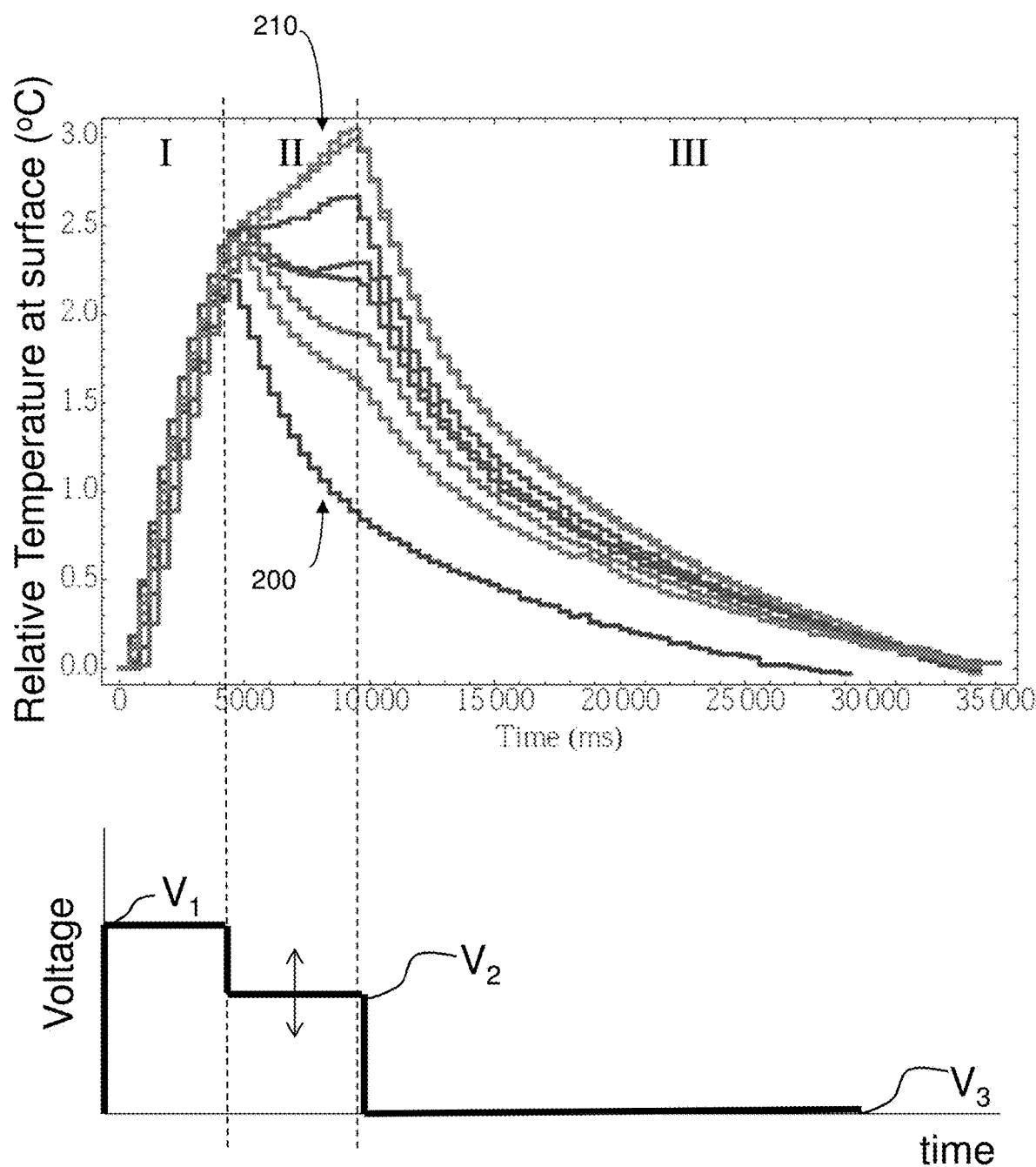
FIG. 8 is an exemplary plot of the relative change in temperature of a surface in response to a set of voltage profiles applied to a device according to some embodiments.
Figure 9:
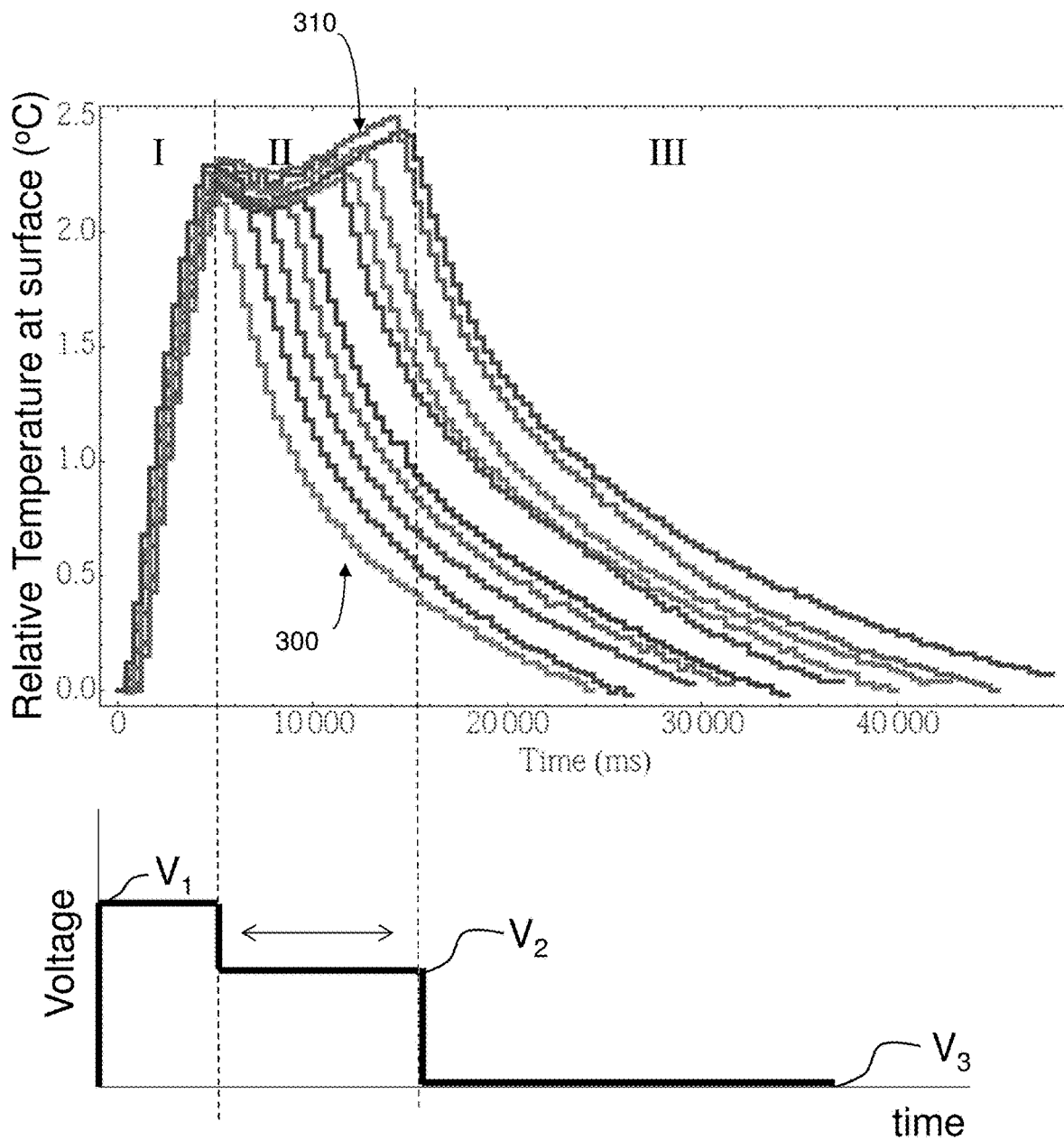
FIG. 9 is an exemplary plot of the relative change in temperature of a surface in response to another set of voltage profiles applied to a device according to some embodiments.

FIGS. 8-9 show a number of temperature measurements at the surface of the thermoelectric. As illustrated in these figures, the voltage applied during the second regime II of the thermal pulse is varied, by magnitude (shown in FIG. 8) and duration (shown in FIG. 9). This demonstrates an ability for the thermal pulse(s) generated at the surface of the skin to be controlled and varied as desired. Accordingly, the temperature profile of a thermal pulse may be appropriately tailored to suit the thermal needs of the user. For example, as noted herein, it can be appreciated that any suitable voltage profile may be applied to the thermoelectric material(s), according to any appropriate pattern.

FIG. 8 shows a group of waveforms where the duration in which the optional second voltage $V_2$ was applied was kept constant, and the magnitude of the second applied voltage $V_2$ was varied. In this example, waveform 200 corresponds to the instance where no second voltage $V_2$ was applied (i.e., second voltage $V_2$ applied was zero) and waveform 210 corresponds to the case where the second voltage $V_2$ is greatest in magnitude amongst the group. As depicted, when the second voltage $V_2$ is effectively zero, the temperature relaxes in accordance with an exponential decay, as if a single square voltage $V_1$ was applied. Though, upon application of a non-zero second voltage $V_2$, the temperature at the surface may still increase, albeit not as sharply as in the case where the initial voltage $V_1$ is applied. When the second voltage $V_2$ is no longer applied, the temperature profile exhibits relaxation decay behavior.

As illustrated in FIG. 9, the magnitude of the optional second voltage $V_2$ was kept constant and the duration of the second applied voltage $V_2$ was varied. In this example, the length of time between the second applied voltage $V_2$ and the third applied voltage $V_3$ was varied between 0 seconds and about 10 seconds. As shown, the waveform 300 corresponds to the instance where no second voltage $V_2$ was applied (applied for 0 seconds) and waveform 310 corresponds to the case where the second voltage $V_2$ is applied for the longest period of time (applied for 10 seconds) amongst the group. As depicted, as the second voltage $V_2$ lasts longer, the temperature at the surface may continue to increase or hover around a particular temperature range. And, as application of the second voltage $V_2$ ceases, the temperature at the surface decays back toward the initial temperature.

In some embodiments, the controller includes a current source, for generating a suitable electrical signal. The current source may apply a current to the thermoelectric material(s), for generating a thermal pulse at the surface of the skin of a user. The magnitude of a current applied to the thermoelectric material(s) at any given point may fall within a suitable range. In some embodiments, the magnitude of a current applied to the thermoelectric material(s) may be between about 0.1 A and about 4.0 A, between about 0.1 A and about 3.5 A, between about 0.1 A and about 3.0 A, between about 0.2 A and about 2.5 A, between about 0.5 A and about 2.0 A, between about 1.0 A and about 2.0 A, between about 0.1 A and about 1.5 A, between about 0.1 A and about 1.0 A, between about 0.5 A and about 1.0 A, between about 0.1 A and about 0.5 A, between about 1.0 A and about 1.5 A, or any other appropriate range. The electrical signal(s) may be applied to the thermoelectric material(s) in accordance with any suitable form or pattern. In some embodiments, the electrical signal(s) may be applied to the thermoelectric material(s) as one or more square waves (i.e., a constant voltage/current applied for a period of time), which may result in a particular rate of temperature change, depending on how the electrical signal is applied. Or, the electrical signal(s) may exhibit more complex behavior, for example, the electrical signal(s) may be applied as a linear ramp function, non-linear, exponential, polynomial function, piecewise function, etc.

As shown in FIGS. 4A-5B, for some embodiments, to initiate the thermal pulse, as provided in regime I, a first square wave voltage is applied to the thermoelectric material(s), resulting in a sharp linear temperature adjustment at the surface of the skin from the first temperature $T_1$ to the second temperature $T_2$. In regime II, a second square wave voltage is applied, the magnitude of which is less than the magnitude of the first square wave, resulting in a relatively constant, insubstantial change in the temperature $T_2$, $T_2'$ at the surface of the skin. In regime III, no voltage is applied, resulting in a thermal adjustment to the third temperature $T_3$, which may be different from the first initial temperature $T_1$ by a small amount/percentage.

As discussed herein, for various embodiments, the sensation of warming or cooling may be enhanced by generating a series of asymmetric thermal pulses (e.g., thermal pulses which have a faster average rate of temperature change on initiation than the average rate of temperature change on return) at the surface of the skin of a user. In some embodiments, steady-state operation of the device may also include generating a series of thermal pulses in succession. That is, during steady-state operation, the temperature profile of thermal pulses generated in succession may be substantially identical.

Figure 7:
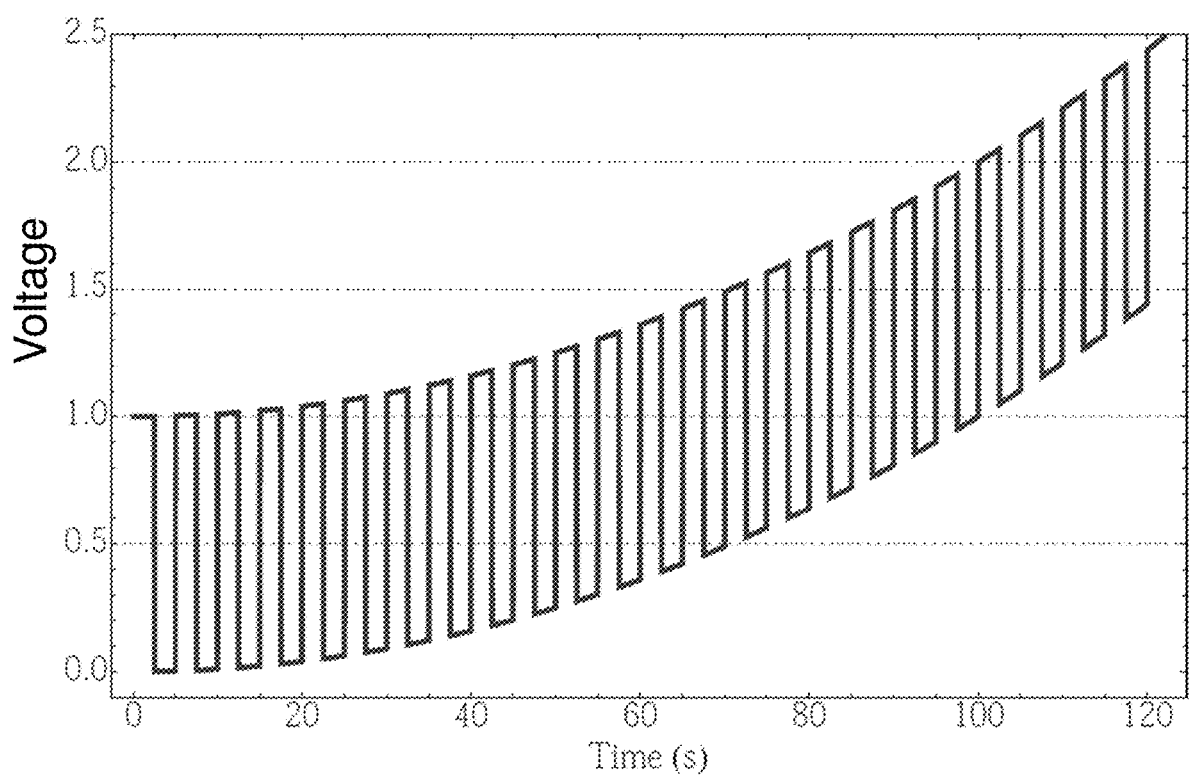
FIG. 7 is an example of an electrical signal applied to a device according to one set of embodiments.

Though, for some embodiments, it may be advantageous to generate non-steady state thermal pulses, which may be suitable to enhance thermal sensation and/or comfort of the user and/or prevent desensitization to temperature changes. For example, in certain embodiments, the duty cycle of the applied signal may be varied. In some embodiments, so as to provide a smooth transition for the user to a steady-state mode of operation, the baseline average of the electrical signal may be gradually increased, as illustrated in FIG. 7, or may gradually decrease, as desired. During non-steady-state operation, the average baseline signal may be adjusted as desired. In some cases, non-steady state operation (i.e., when operation of the device is first initiated, or when more/less power is applied to the thermoelectric at a given time) may allow for an increased amount of cooling or heating at the surface (e.g., more than the device may be designed to dissipate) for a temporary period of time.

In certain embodiments, the controller may apply an electrical signal to the thermoelectric material(s) according to a suitable duty cycle. The term duty cycle as known in the art generally refers to the percentage of a time period in which an electrical signal is active. In various embodiments, the electrical signal applied to the thermoelectric material(s) by the controller may exhibit a duty cycle of between about 10% and about 50%, greater than or equal to about 10%, greater than or equal to about 20%, greater than or equal to about 30%, greater than or equal to about 40%, or greater than or equal to about 50%. In some embodiments, the duty cycle applied by the controller may be less than about 50%, less than about 40%, less than about 30%, less than about 20%, or less than about 10%. Combinations of the above referenced ranges are also possible (e.g., between about 10% and about 50%).

As will be understood by those skilled in the art, the particular ranges of electrical signal (i.e., voltages, currents) are non-limiting and may suitably vary depending, in part, on the overall configuration of the device, particular materials selected (e.g., thermoelectric materials, number of thermoelectric materials), intrinsic resistances of various components within the device, or other aspects that may contribute to the functionality of the device.

As noted above, the thermal adjustment portion of the device may include one or more thermoelectric materials. The thermoelectric materials may, in some embodiments, be preferable for generating rapid, reversible thermal transients (i.e. thermal pulses). Non-limiting examples of suitable thermoelectric materials may include columns of p-type and n-type doped semiconductor materials, bismuth chalcogenides (e.g., $Bi_2Te_3$, $Bi_2Se_3$), lead selenide, Si—Ge alloys, skutterudites (e.g., including the formula $LM_4X_{12}$, wherein L is a rare earth metal, M is a transition metal, and X is a metalloid), or any other suitable thermoelectric materials.

The thermoelectric material(s) may have any suitable thickness. For example, in some embodiments, the thickness may be selected such that the thermoelectric material(s) may be comfortably held against the wrist, arm, leg, ankle, neck, or any other suitable part of the body. In some embodiments, the thickness of each of the thermoelectric materials may be between about 1 millimeter and about 5 millimeters (e.g., between about 1 millimeter and about 3 millimeters). Other thicknesses are also possible.

In some embodiments, each of the thermoelectric materials, or modules that include the thermoelectric material(s), may have a largest average cross-sectional dimension of between about 10 mm and about 4 cm (e.g., between about 30 mm and about 500 mm). Other average cross-sectional dimensions are also possible. Those skilled in the art would be capable of selecting an appropriate size for the thermoelectric material based upon the configuration of the device.

Thermoelectric materials, or modules thereof, may be provided in any suitable configuration. For example, a module may include thermoelectric materials sandwiched between ceramic plates, in some cases, for protection and support, as well as to provide thermal conductivity to the surface of the skin.

Referring back to FIGS. 2-3, for some embodiments, the device may include a thermally insulative material 122 that is positioned so as to cover the thermoelectric material(s) 110. In certain embodiments, during use, the thermoelectric material(s) may be located between the thermally insulative material and the surface of the skin. The thermally insulative material may be effective to retain the level of heat (or cooling) generated by the thermoelectric material(s), adjacent the surface.

In some embodiments, the thermally insulative material may increase the overall magnitude of temperature change for a given electrical signal, as compared to the use of thermally conductive materials. As a result, incorporation of a thermally insulative material may give rise to stronger or otherwise enhanced thermal pulsing, for example, increasing the overall sensation of temperature change for a user, and/or a reduction in power consumption by the device.

Figure 10:
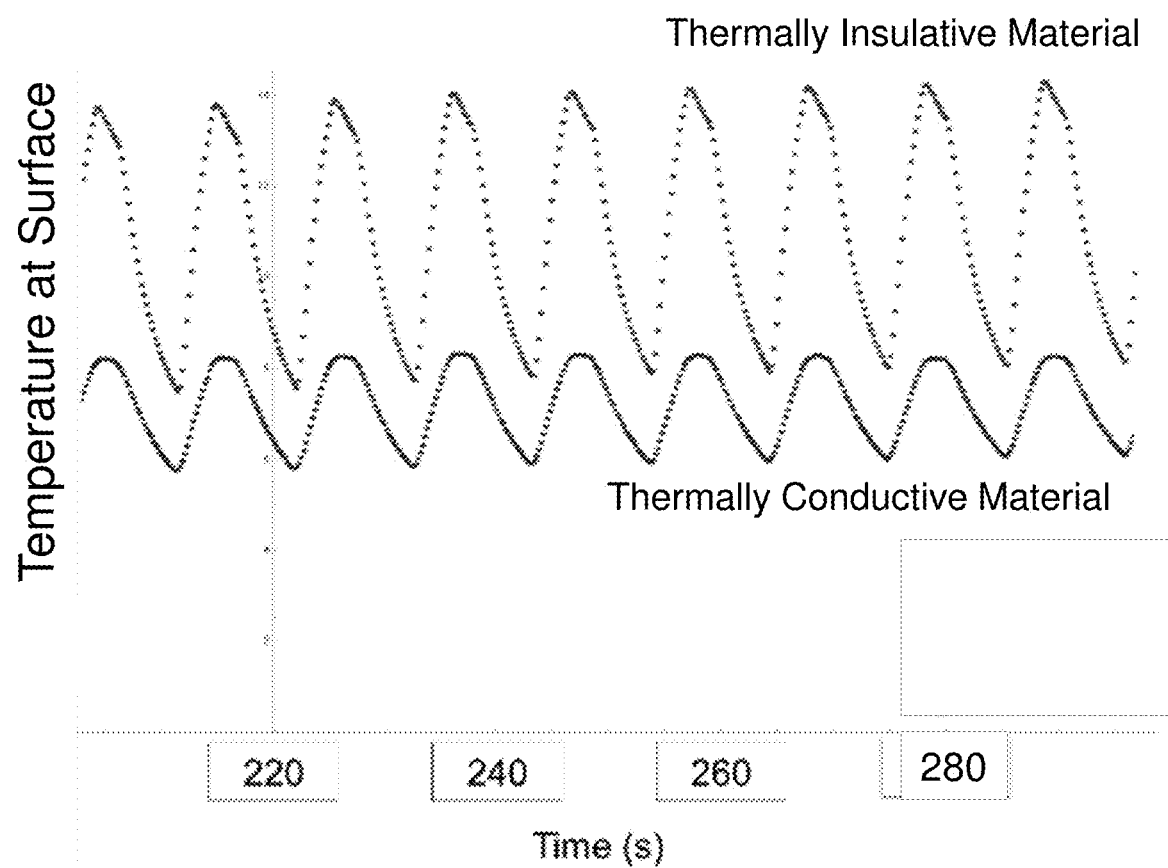
FIG. 10 is an exemplary plot of the temperature of a surface for a series of thermal pulses generated by two devices according to some embodiments.

FIG. 10 depicts an example where a series of thermal heating pulses are observed, with the same application of electrical signal, for a thermoelectric material covered by a thermally insulative material (e.g., neoprene), as compared to a thermoelectric material covered by a thermally conductive material (e.g., aluminum, other metal(s)). For the device incorporating the thermally insulative material, the regimes of temperature adjustment are more pronounced than for the device incorporating the thermally conductive material. That is, the rates of temperature change are more abrupt for the device incorporating the thermally insulative material; and the average magnitude of temperature increase is also greater for the device that includes the thermally insulative material.

Though, for certain embodiments, it may be preferable for the device to incorporate a thermally conductive material, for example, for thermal dissipation of the generated heating or cooling. For example, it may be desirable to switch rapidly between heating and cooling modes. Accordingly, the ability to dissipate heat may allow for residual heating or cooling to be reduced.

Any suitable dissipation unit may be employed, for example, a heat sink, a fan, a phase change material, a heat exchanger, or combinations thereof. In some embodiments, the thermal dissipation unit has a size and/or weight such that it can be mounted comfortably on the device and, in turn, for example, on a wrist, as illustrated in FIGS. 1A-1C.

As described above, in some embodiments, the device includes a suitable power source. The power source may include any appropriate materials, such as one or more batteries, photovoltaic cells, etc. Non-limiting examples of suitable batteries include Li-polymer (e.g., with between about 100 and about 1000 mAh of battery life), Li-ion, nickel cadmium, nickel metal hydride, or the like. In some cases, the battery may output a constant voltage and the controller may be configured to apply an appropriate degree of pulse-width modulation to generate time-varying voltage profiles.

The device may be further configured to use relatively low amounts of power, in contrast with HVAC systems or other localized electronic thermal sources such as heaters, fans, or the like.

In certain embodiments, the device may include one or more sensors arranged to collect information at the region of the thermoelectric material(s) adjacent the surface. Any suitable sensor(s) may be employed, for example, temperature sensors (e.g., thermistors, thermocouples), humidity and/or moisture sensors, barometers, etc., in any appropriate configuration. In some embodiments, the device includes one or more temperature sensors for monitoring the temperature at the surface of the thermoelectric material(s) and/or skin. For example, if the temperature measured at the surface of the thermoelectric material(s) and/or skin exceeds or is lower than a desired temperature, the sensor may send a signal to the controller to adjust the applied electrical signal (e.g., apply a negative (or lower) voltage to reduce the temperature, apply a positive (or higher) voltage to increase the temperature) to result in a preferred temperature profile.

In some embodiments, the temperature sensor may be incorporated with the controller, for monitoring the temperature of the controller. In certain embodiments, one or more temperature sensors may be placed directly adjacent one or more surfaces of the thermoelectric material(s). In some embodiments, the temperature sensor(s) may be arranged for sensing the temperature of ambient air. In some embodiments, the temperature sensor(s) may measure the temperature difference across different components of the device (e.g., between the surface of the skin and the thermoelectric material(s), between the thermoelectric material(s) and ambient air). The temperature sensor(s), in some embodiments, may be configured with the controller to operate in accordance with a feedback loop, for example, to prevent excessive heating or cooling of the device and/or to maintain the temperature at the surface within a preferred range.

The device may include additional control features, as desired, for example, wireless capabilities for enabling suitable communication with other devices/systems (e.g., for controlling aspects of the device, controlling/monitoring the temperature at the surface of the skin, etc.). Wireless devices are generally known in the art and may include, in some cases, wifi and/or Bluetooth systems.

Having thus described several aspects of at least one embodiment of the present disclosure, it is to be appreciated various alterations, modifications, and improvements will readily occur to those skilled in the art. In some embodiments, the device may be used for therapeutic applications. For instance, the device may be used to alleviate hot flashes (e.g., during pregnancy, during menopause), or provide thermal comfort in humid or arid environments. Such alterations, modification, and improvements are intended to be part of this disclosure, and are intended to be within the spirit and scope of the present disclosure. Accordingly, the foregoing description and drawings are by way of example only.

What is claimed is:

1. A device for manipulating a temperature of a surface, comprising:
   a thermal adjustment apparatus including a thermoelectric material constructed and arranged to be disposed adjacent the surface, the thermal adjustment apparatus configured to generate a plurality of thermal pulses in succession at a region of the thermal adjustment apparatus adjacent the surface, wherein the plurality of thermal pulses cycle a temperature of the region between at least a first temperature and a second temperature, wherein the thermal adjustment apparatus is configured to be worn on a neck or wrist of a wearer, wherein the surface is a skin surface of the wrist or the neck of the wearer; and
   a controller configured to control the thermal adjustment apparatus to generate the plurality of thermal pulses, wherein the controller is configured to control the thermal adjustment apparatus such that the plurality of thermal pulses include a first temperature adjustment from the first temperature to the second temperature at an average rate of temperature change between 0.1° C./sec and 10.0° C./sec over a first time period between 1 second and 10 seconds, and a second temperature adjustment from the second temperature to the first temperature over a second time period longer than the first time period, and wherein a difference in magnitude between the first temperature and the second temperature is less than 10° C.

2. The device of claim 1, wherein the second temperature adjustment exhibits relaxation decay.

3. The device of claim 1, wherein each of the thermal pulses occurs over a total time period greater than 60 seconds and less than or equal to 120 seconds.

4. The device of claim 3, wherein each of the thermal pulses occurs over a total time period greater than 60 seconds and less than or equal to 90 seconds.

5. The device of claim 1, wherein the difference in magnitude between the first temperature and the second temperature is less than 5° C.

6. The device of claim 1, wherein the first temperature and the second temperature are different from an initial surface temperature.

7. The device of claim 6, wherein the first temperature and/or the second temperature are greater than the initial surface temperature.

8. The device of claim 6, wherein the first temperature and/or the second temperature are less than the initial surface temperature.

9. The device of claim 6, wherein the first temperature and the second temperature are not constant.

10. The device of claim 1, wherein the average rate is between approximately 0.5° C./sec and 1° C./sec.

11. The device of claim 1, further comprising:
a housing configured to be worn on the wrist or the neck of the wearer, wherein the thermal adjustment apparatus is disposed on the housing; and
a battery disposed in the housing configured to provide power to the thermal adjustment apparatus.

12. The device of claim 11, further comprising a band configured to secure the housing to the wrist or the neck of the wearer.

13. The device of claim 1, wherein the average rate is a first average rate having a first magnitude, wherein the second temperature adjustment from the second temperature to the first temperature is at a second average rate of temperature change having a second magnitude that is less than the first magnitude.

14. A device for manipulating a temperature of a surface, comprising:
a thermal adjustment apparatus including a thermoelectric material constructed and arranged to be disposed adjacent the surface, the thermal adjustment apparatus configured to generate a plurality of thermal pulses in succession at a region of the thermal adjustment apparatus adjacent the surface, wherein the plurality of thermal pulses cycle a temperature of the region between at least a first temperature and a second temperature, wherein the thermal adjustment apparatus is configured to be worn on a neck or wrist of a wearer, wherein the surface is a skin surface of the wrist or the neck of the wearer; and
a controller configured to control the thermal adjustment apparatus to generate the plurality of thermal pulses, wherein the controller is configured to control the thermal adjustment apparatus such that the plurality of thermal pulses include a first temperature adjustment from the first temperature to the second temperature at an average rate of temperature change between 0.1° C./sec and 10.0° C./sec over a first time period between 1 second and 30 seconds, and a second temperature adjustment from the second temperature to the first temperature over a second time period longer than the first time period, wherein the second temperature adjustment exhibits relaxation decay, and wherein a difference in magnitude between the first temperature and the second temperature is less than 10° C.

15. The device of claim 14, wherein each of the thermal pulses occurs over a total time period greater than 60 seconds and less than or equal to 120 seconds.

16. The device of claim 15, wherein each of the thermal pulses occurs over a total time period greater than 60 seconds and less than or equal to 90 seconds.

17. The device of claim 14, wherein the difference in magnitude between the first temperature and the second temperature is less than 5° C.

18. The device of claim 14, wherein the first temperature and the second temperature are different from an initial surface temperature.

19. The device of claim 18, wherein the first temperature and/or the second temperature are greater than the initial surface temperature.

20. The device of claim 18, wherein the first temperature and/or the second temperature are less than the initial surface temperature.

21. The device of claim 14, wherein the first temperature and the second temperature are not constant.

22. The device of claim 14, wherein the average rate is between approximately 0.5° C./sec and 1° C./sec.

23. The device of claim 14, further comprising:
a housing configured to be worn on the wrist or the neck of the wearer, wherein the thermal adjustment apparatus is disposed on the housing; and
a battery disposed in the housing configured to provide power to the thermal adjustment apparatus.

24. The device of claim 23, further comprising a band configured to secure the housing to the wrist or the neck of the wearer.

25. The device of claim 14, wherein the average rate is a first average rate having a first magnitude, wherein the second temperature adjustment from the second temperature to the first temperature is at a second average rate of temperature change having a second magnitude that is less than the first magnitude.

* * * * *